(12) United States Patent
Turgeon et al.

(10) Patent No.: US 12,159,723 B2
(45) Date of Patent: Dec. 3, 2024

(54) POPULATION-BASED MEDICATION RISK STRATIFICATION AND PERSONALIZED MEDICATION RISK SCORE

(71) Applicants: Jacques Turgeon, Philadelpia, PA (US); Veronique Michaud, Orlando, FL (US); Brian Cicali, Gainesville, FL (US)

(72) Inventors: Jacques Turgeon, Philadelpia, PA (US); Veronique Michaud, Orlando, FL (US); Brian Cicali, Gainesville, FL (US)

(73) Assignee: Tabula Rasa Healthcare, Inc., Moorestown, NJ (US)

( * ) Notice: Subject to any disclaimer, the term of this patent is extended or adjusted under 35 U.S.C. 154(b) by 293 days.

(21) Appl. No.: 16/760,631

(22) PCT Filed: Oct. 31, 2018

(86) PCT No.: PCT/US2018/058405
§ 371 (c)(1),
(2) Date: Apr. 30, 2020

(87) PCT Pub. No.: WO2019/089725
PCT Pub. Date: May 9, 2019

(65) Prior Publication Data
US 2021/0375486 A1     Dec. 2, 2021

Related U.S. Application Data

(60) Provisional application No. 62/611,975, filed on Dec. 29, 2017, provisional application No. 62/579,328, filed on Oct. 31, 2017.

(51) Int. Cl.
*G16H 70/40*     (2018.01)
*G16H 10/60*     (2018.01)
(Continued)

(52) U.S. Cl.
CPC ............. *G16H 70/40* (2018.01); *G16H 10/60* (2018.01); *G16H 20/10* (2018.01); *G16H 50/30* (2018.01); *G16H 50/70* (2018.01)

(58) Field of Classification Search
CPC ........ G16H 70/40; G16H 50/30; G16H 50/70; G16H 20/10
See application file for complete search history.

(56) References Cited

U.S. PATENT DOCUMENTS 8,744,872 B1    6/2014   Mehta et al.
2008/0082582 A1   4/2008   Jung
(Continued)

FOREIGN PATENT DOCUMENTS

EP          2339488 A1    6/2011
WO    2008060287 A1    5/2008

OTHER PUBLICATIONS

International Search Report mailed Jan. 23, 2019 in connection with International Patent Application No. PCT/US2018/058405.
(Continued)

*Primary Examiner* — Stella Higgs
(74) *Attorney, Agent, or Firm* — Morgan, Lewis & Bockius LLP

(57) ABSTRACT

Embodiments of the invention relate to a system and method for population-based medication risk stratification and for generating a personalized medication risk score. The system and method may pertain to a software that relates pharmacological characteristics of medications and patient's drug regimen data into algorithms that (1) enable identification of high-risk patients for adverse drug events within a population distribution, and (2) allow computation of a personalized medication risk score which provides personalized, evidence-based information for safer drug use to mitigate medication risks.

17 Claims, 17 Drawing Sheets

(51) Int. Cl.
    *G16H 20/10*     (2018.01)
    *G16H 50/30*     (2018.01)
    *G16H 50/70*     (2018.01)

(56) References Cited

U.S. PATENT DOCUMENTS

| | | | |
|---|---|---|---|
| 2008/0126117 A1* | 5/2008 | Miller | G16H 20/10 705/2 |
| 2010/0223068 A1* | 9/2010 | Von Schweber | G06Q 50/22 705/2 |
| 2012/0010217 A1* | 1/2012 | Du | A61P 37/08 514/255.04 |
| 2014/0222400 A1* | 8/2014 | Coleman | G16H 20/10 703/2 |
| 2015/0178465 A1 | 6/2015 | Knowlton | |

OTHER PUBLICATIONS

Written Opinion mailed Jan. 23, 2019 in connection with International Patent Application No. PCT/US2018/058405.
Extended European Search Report for corresponding European Patent Application No. 18873693.8 dated Jul. 5, 2021, 10 pages.
Hilmer Sarah N et al, "A Drug Burden Index to Define the Functional Burden of Medications in Older People", Archives of Internal Medicine, American Medical Association, vol. 167, No. 8, (Apr. 23, 2007), pp. 781-787.
Office Action for related Singapore Patent Application No. 11202003873W dated Jul. 21, 2022, 7 pages.

\* cited by examiner

| | Risk Score |
|---|---|
| 0 Med | 0 |
| 1-5 Meds | 1 |
| 6-10 Meds | 3 |
| 11-15 Meds | 6 |
| 16-21 Meds | 9 |
| 22+ Meds | 12 |
| Anticholinergic Burden score | Actual value of ACB score (i.e. ACB score = 6 then Risk score = 6) MAXIMUM Score = 6 |
| Sedative Burden Score | Actual value of SB score (i.e. SB score = 3 then Risk score = 3) MAXIMUM Score = 5 |
| Competitive inhibition: INHIBITOR and SUBSTRATE | 5 MAXIMUM SCORE = 5 |
| Competitive inhibition: INDUCER and SUBSTRATE | 5 MAXIMUM SCORE = 5 |
| Competitive inhibition: 3 SUBSTRATES SAME ISOENZYME | 3 MAXIMUM SCORE = 6 |
| Competitive inhibition: 2 SUBSTRATES SAME ISOENZYME | 2 MAXIMUM SCORE = 4 |
| LQTS SCORE | 0-4 = 0 4.5-7.5 = 2 8-11 = 5 11.5-15 = 7 15+ = 10 |
| Pharmacogenomics CYP2D6 substrates | 5 MAXIMUM SCORE = 5 |
| Pharmacogenomics CYP2C19 substrates | 3 MAXIMUM SCORE = 3 |
| Pharmacogenomics CYP2C9 substrates | 3 MAXIMUM SCORE = 3 |
| Pharmacogenomics CYP3A4 substrates | 2 MAXIMUM SCORE = 1 |
| RENAL FUNCTION (TBD) | MAXIMUM SCORE 10 |
| TOTAL SCORE | Add all individual Risk Score values (Maximum score is 75) |

FIG. 7

| Risk Factor | Percentiles at high risk | Number of Patients |
|---|---:|---:|
| Total Risk Score | 10.14% | 30633 |
| Medication Count | 13.91% | 42045 |
| Cognitive Impairment | 9.11% | 27521 |
| Sedation | 11.78% | 35610 |
| Heart-Rhythm Impairment | 2.60% | 7847 |
| Competitive Inhibition | 11.19% | 33813 |

FIG. 8

PATIENT INFORMATION eMTM Date: 5/6/2016
First Name: ___  Last Name: ___  DOB: 09/15/1948 (67 years)  Prescriber: ___
Gender: Male  Race: White or Caucasian  MRPs: Not Specified  Location: TFP
Estimated CrCl: UNKNOWN  Adherence Score: 1=Medium Adherence MRPs = medication-related problems

EXECUTIVE SUMMARY OF RECOMMENDATIONS: [PLEASE REFER TO PAGE 5 FOR FULL RATIONALE]

1. Decrease dose or discontinue Canagliflozin due to renal impairment.
   - ☐ ACCEPT RECOMMENDATION
   - ☐ ACCEPT WITH CHANGES: ___
   - ☐ NO CHANGE - AWARE OF RECOMMENDATION 2. Consider discontinuing proton pump inhibitor therapy (via step down therapy) or, at minimum, decreasing the dose of pantoprazole.
   - ☐ ACCEPT RECOMMENDATION
   - ☐ ACCEPT WITH CHANGES: ___
   - ☐ NO CHANGE - AWARE OF RECOMMENDATION 3. Consider replacing Metoprolol with Bisoprolol as an alternative due to a (a) drug-gene interaction, and (b) drug-drug interaction.
   - ☐ ACCEPT RECOMMENDATION
   - ☐ ACCEPT WITH CHANGES: ___
   - ☐ NO CHANGE - AWARE OF RECOMMENDATION

GENETIC RESULTS SNAPSHOT

| ATM | CYP4F2 |
|---|---|
| CYP2C19 | SLCO1B1 |
| CYP2C9 | TPMT |
| CYP2D6 | VCORC1 |
| CYP3A4 | CYP3A5 |
|  | ApoE |

Thrombosis Profile:

| F2 | F5 | MTHFR (A>C) | MTHFR (C>T) |
|---|---|---|---|

| No variant | 1 variant |
|---|---|
| ≥1 [decreased] variants | ≥1 [increased] variants |

|  | PRE-INTERVENTION | IF ALL RECOMMENDATIONS ACCEPTED |
|---|---|---|
| Total Meds: | 16 | 14 |
| Chronic Meds: | 16 | 14 |
| ACB Score: | 2 | 1 |
| SB Score: | 3 | 2 |
| Renal Function: | UNKNOWN | UNKNOWN |
| LQTS Score: | 0 | 0 |
| Competitive Inhibition: | 7 | 3 |
| Total Risk Score: | 21 | 12 |

| Low Risk |  |  | High Risk |
|---|---|---|---|

Prescriber Signature: ___

FIG. 10

POPULATION-BASED MEDICATION RISK STRATIFICATION AND PERSONALIZED MEDICATION RISK SCORE

CROSS-REFERENCE TO RELATED APPLICATIONS

This application is a U.S. National Stage application of International Patent Application No. PCT/US2018/058405 filed Oct. 31, 2018, which claims the benefit of priority of U.S. Provisional Application No. 62/611,975 filed Dec. 29, 2017, and U.S. Provisional Application No. 62/579,328, filed Oct. 31, 2017, which applications are incorporated by reference herein, in their entireties and for all purposes.

BACKGROUND

Medications are vital for the prevention and treatment of diseases, illnesses, disabilities and death. However due to the biologically active nature of medications they can also cause bodily harm, especially when multiple medications are taken simultaneously, a condition described as polypharmacy. Patients with polypharmacy are at a known risk for multi-drug interactions which can lead to adverse drug events responsible for negative changes in quality of life and even death. Due to this, the prediction of potential multi-drug interactions and adverse drug events are a major focus for drug developers, so much so that the FDA requires all drug-labels to report known interactions with other medications. Even still, multi-drug interactions and adverse drug events continue to cause health and financial issues for patients and their care providers. According to a report from the Centers for Medicare and Medicaid Services (CMS) in 2014, adverse drug events cause 125,000 hospitalizations, 1 million emergency department visits, 3.5 million doctor's office visits and more than 100,000 deaths per year. With these numbers in mind, better methods to estimate the risk associated with drug intake are required.

A plethora of clinical data has been generated concerning the causes of adverse drug events. One of these data sources is multi-drug interactions due to a hindered capacity to excrete or metabolize drugs. For instance, the FDA, CDER and US Department of Health and Human Services have published guidelines on how to study and report drug metabolism characteristics and drug interactions. Drug metabolism is the body's form of defense that is responsible for excreting toxins, such as medications, out of the body. The guidelines mentioned above focus mostly on characterizing singular medication's metabolic pathways within the body. These characterization results are then compared to other singular medication characterizations and conclusions are made. If two drugs share the same metabolic pathway then it is concluded that they interact with each other, a condition termed Competitive Inhibition. One drug to one drug interaction studies are then required to determine the extent of drug interaction through competitive inhibition for these two drugs. Even with this system in place, forty-five to fifty million adverse drug events are observed per year in the US. In fact, adverse drug events represent the fourth leading cause of death in the United States. A major reason for this is the current methodology for predicting multi-drug interactions is immensely complex when a patient is taking multiple medications at once. For example, if a patient is taking twelve medications due to multiple health issues, sixty-six singular drug-drug pairs need to be examined for interaction potential. Since there are only a few pathways that drugs are metabolized within the body, competitive inhibition and thus multi-drug interactions are unavoidable in these cases. One of the aspects of this presented invention is to take advantage of developed techniques to identify and then analyze these multi-drug interactions (Patent Application No. 62/111,707, filed on Feb. 4, 2015, entitled "Medication Risk Mitigation Matrix System and Method," and patent application Ser. No. 15/008,555, filed on Jan. 28, 2016, entitled "Medication Risk Mitigation Matrix System and Method," which are incorporated by reference herein in their entireties, and may be referred to hereinafter as "the '707 application" and "the '555 application", respectively) and, in an innovative method not yet discovered within the industry, to attribute a quantitative risk score value to multi-drug interactions observed within a patient's drug regimen.

Adverse drug events are not only caused by competitive inhibition of metabolic pathways. For instance, there are multiple tools available to measure varying aspects of medication risk available that are outside of competitive inhibition. These tools include the Drug Burden Index, Sedative Load Model, Tool 3I for Medication Fall Risk, Opioid Risk Tool, and the Beers Criteria, to just name a few. There remains a need for systems that measure and stratify risk of the occurrence of adverse drug events due to a particular medication regimen.

SUMMARY

Embodiments of the invention described herein generally relate to a system and method for population based medication risk stratification and for generating a personalized medication risk score. In some embodiments, the system and method may pertain to the development of a software that relates pharmacological characteristics of medications and patient's drug regimen data into algorithms that (1) enable identification of high-risk patients for adverse drug events within a population distribution, and (2) allow computation of a personalized medication risk score which provides personalized, evidence-based information for safer drug use to mitigate medication risks. Each part of these embodiments of the invention contributes to the recognition of the risk of drug-related adverse events and empowers a care provider to mitigate the harm arising from taking multiple medications, including prescription, over-the-counter, and herbal products.

Embodiments of the invention described herein generate a Medication Risk Score for Drug-induced Long QT Syndrome and potentially lethal cardiac arrhythmias. The newly developed algorithms which are part of this invention utilize, in part, information from developed proprietary information (U.S. Provisional Application No. 62/338,704, filed May 19, 2016, entitled "Methods of Treatment Having Reduced Drug-Related Toxicity and Methods of Identifying Patient Harm Arising from Prescribed Medications," and International Application No. PCT/US2017/033539, filed on May 19, 2017, entitled "Methods of Treatment Having Reduced Drug-Related Toxicity and Methods of Identifying The Likelihood of Patient Harm Arising from Prescribed Medications", which are incorporated by reference herein in their entireties, and may be referred to hereinafter as "the '704 application" and "the '539 application", respectively).

In brief, embodiments of the invention described herein include algorithms that look at multiple factors that influence a medication regimen's likelihood of causing a negative health effect. The following factors are used to drive the software's algorithms to determine risk in respect to patient's medication regimen:

The number of prescribed medications

The indices of anticholinergic burden

The indices of sedation effects

The risk of QT-interval prolongation

The Competitive Inhibition of the regimen

The combinatorial assessment of these individual risk factors provides a comprehensive approach to medication risk stratification at a population level as well as the possibility of personalized medication risk mitigation at the individual level by interpreting a Personalized Medication Risk Score. Hence, the output of this assessment is a quantitative score that can be used to measure and stratify risk of the occurrence of adverse drug events due to a particular medication regimen. This quantitative score also allows the identification of patients at higher risk for multi-drug interactions within a population, and thus require medication risk mitigation more so than others. This identification ability is of high importance for care providers who seek to know which of their patients require immediate attention. Once these patients are recognized, the software tool provides a personalized snapshot of the risk factors described above, empowering the provider to mitigate their medication risk accurately and efficiently.

To ensure the accuracy of the invention described herein, the scoring mechanisms have been validated against literature and clinical cases. The software has been applied to various healthcare population settings numbering approximately 800,000 patients. In these applications various high-risk groupings were identified and criteria were generated for patients of the highest-risk through statistical aggregation. The tool has been found to typically identify the top 15 to 20 percent of high risk patients for each risk factor as well as identify the approximate top 5 to 15 percent of the population considered at highest risk. Not only were high risk members of the population identified, but the embodiments of the invention generated personalized medication risk score snapshots, which empower health professionals to generate recommendations which mitigate the established risks According to embodiments of the invention described herein, the advantages are obtained by using a method for estimating the risk of medication-related problems due to medication characteristics in accordance with a patient's overall medication regimen. The invention allows for the creation of personalized, evidence-based recommendations for healthcare providers. Once determined using the invention, the risk of medication-related problems can be quantitatively compared to identify high-risk patients within a population.

Concerning one aspect of the invention, the method utilizes a non-transitory computer readable storage media having program instructions stored in a memory device. The instructions are executable by a processor to direct the performance of operations to estimate patient medication-related risk. The program instructions for determining the medication-related risk scoring may include one or more of the following steps:

Importing a first data set comprising patient-specific drug regimens, converting the medication data into their respective active ingredients, quantifying the number of active ingredients each patient-specific regimen contains, and assigning an aggregated risk score. According to an alternative embodiment, this step includes importing a first data set comprising patient-specific drug regimens, converting the medication data into their respective active ingredients, associating the respective active ingredients with their risk of one or more side effects (e.g., by utilizing data from the FDA Adverse Event Reporting System), and assigning an aggregated risk score.

Importing a second data set comprising the indices of anticholinergic burden, associating the respective active ingredients with their clinically determined anticholinergic value, quantifying the value for the entire respective regimen, and assigning an aggregated risk score.

Importing a third data set comprising the indices of sedation effects, associating the respective active ingredients with their clinically determined sedation value, quantifying the value for the entire respective regimen, and assigning an aggregated risk score.

Importing a fourth data set comprising the indices of QT-prolongation risk, associating the respective active ingredients with their clinically determined QT-risk value, quantifying the value for the entire respective regimen, and assigning an aggregated risk score.

Importing a fifth data set comprising the metabolic pathways and extent of metabolism for each active ingredient, associate the respective ingredients with competitive inhibition values based on shared pathways, quantifying the competitive inhibition value for the entire respective regimen, and assigning an aggregated risk score.

The datasets outline above are processed by 5 pre-defined algorithms to calculate a patient-specific medication risk stratification score for each factor. The factor scores are then combined to determine a Personalized Medication Risk Score.

Following the above operations, according to another aspect of the invention, personalized medication risk mitigation snapshots are generated for each medication regimen that is analyzed. The snapshot is generated by assembling the outputs of the processing instructions between each risk factor data set and algorithm. These snapshots provide a personalized overview of each patient's medication-related risk. The snapshot empowers a healthcare professional to provide accurate, evidence based medication risk mitigation recommendations.

In accordance with another aspect of the invention, each medication risk factor score and the total medication risk score of each medication regimen is compiled into a data set. The compiled data set is then statistically aggregated by risk factor score criteria into high and low risk groups based on literature and clinical observations. The high-risk groups are then analyzed by repeat string search to categorize those members who are included in all high-risk groups. Typically, the output is approximately 5 to 15 percent of the population, who are considered at most risk for medication related problems including, but not limited to, adverse drug events.

In an embodiment, the invention includes a method of treating a patient who is identified as being at high risk for an adverse drug event, wherein the patient has been prescribed a drug regimen that includes at least a first drug and a second drug, the method includes one or more of the steps of:

(a) removing the first drug and/or the second drug from the patient's drug regimen;

(b) reordering which of the first drug and the second drug is taken first by the patient;

(c) changing the timing of when the first drug and/or the second drug are taken by the patient;

(d) changing time of day when the first drug and/or the second drug are taken by the patient;

(e) replacing the first drug and/or the second drug of the patient's drug regimen with one or more alternate drugs of the same class and/or category as the first drug and/or the second drug;

(f) reducing the dosage of the first drug and/or the second drug from an initial dosage to a reduced dosage;

(g) increasing the dosage of the first drug and/or the second drug from an initial dosage to an increased dosage;

(h) performing a surgical procedure; and (i) adding at least a third drug to the patient's drug regimen;

wherein the one or more steps are provided to reduce the patient's high risk of the adverse drug event.

Another embodiment of the present invention provides a non-transitory computer-readable medium with instructions stored thereon, that when executed by a processor, perform a method (e.g., a computer program product may be embodied in the non-transitory computer readable storage medium and comprise computer instructions for carrying out the method). According to an embodiment, the computer-implemented method comprises calculating an aggregated risk factor score representative of each of one or more risk factors, two or more risk factors, three or more risk factors, four or more risk factors, or five or more risk factors associated with a patient's drug regimen; and combining the aggregated risk factor scores calculated for each of the risk factors to provide a quantitative personalized medication risk score that is representative of the patient's risk for an adverse drug event. According to an embodiment, the risk factors are selected from the group consisting of:

1) number of active ingredients in the drug regimen,
2) anticholinergic burden of the active ingredients in the drug regimen,
3) sedative burden of the active ingredients in the drug regimen,
4) QT-interval prolongation risk of the active ingredients in the drug regimen, and
5) competitive inhibition of the active ingredients in the drug regimen.

According to an embodiment, the method also provides a data set representative of a patient population's risk of an adverse drug event.

According to an embodiment, the method provides the relative risk of each of the risk factors with respect to each other. For example, the method may provide the quantitative personalized medication risk score as a visual representation of a relative risk of each of the risk factors with respect to each other. As described herein, a clinician may adjust a patient's drug regimen by lowering the risk associated with those factors that pose a higher risk relative to the other risk factors.

According to an embodiment, calculating the aggregated risk factor score representative of the number of active ingredients in the drug regimen comprises importing (e.g., receiving) a data set comprising patient-specific drug regimens, converting said data set into respective active ingredients, quantifying the number of active ingredients each patient-specific regimen contains, and assigning the risk factor score representative of the number of active ingredients in the drug regimen.

According to an embodiment, calculating the aggregated risk factor score representative of the anticholinergic burden of the active ingredients in the drug regimen comprises importing (e.g., receiving) a data set comprising indices of anticholinergic burden, associating the respective active ingredients with their clinically determined anticholinergic value, quantifying the value for the entire respective regimen, and assigning the aggregated risk factor score representative of the anticholinergic burden of the drug regimen.

According to an embodiment, calculating the aggregated risk factor score representative of the sedative burden of the active ingredients in the drug regimen comprises importing (e.g., receiving) a data set comprising indices of sedation effects, associating the respective active ingredients with their clinically determined sedation value, quantifying the value for the entire respective regimen, and assigning the aggregated risk factor score representative of the sedative burden of the drug regimen.

According to an embodiment, calculating the aggregated risk factor score representative of the QT-interval prolongation risk of the active ingredients in the drug regimen comprises importing (e.g., receiving) a data set comprising indices of QT-prolongation risk, associating the respective active ingredients with their clinically determined QT-risk value, quantifying the value for the entire respective regimen, and assigning the aggregated risk factor score representative of the QT-interval prolongation risk of the drug regimen.

According to an embodiment, calculating the aggregated risk factor score representative of the competitive inhibition of the active ingredients in the drug regimen comprises importing (e.g., receiving) a data set comprising metabolic pathways and extent of metabolism for each active ingredient, associating the respective ingredients with competitive inhibition values based on shared pathways, quantifying the competitive inhibition value for the entire respective regimen, and assigning the aggregated risk factor score representative of the competitive inhibition of the drug regimen.

According to an embodiment, the invention provides a processor configured to implement the non-transitory computer-readable medium with instructions stored thereon.

According to an embodiment, the invention provides a client device comprising the processor, a communication infrastructure, a memory, a user interface and a communication interface.

According to an embodiment, the invention provides a system comprising one or more computing devices, the one or more computing devices comprising one or more processors configured to implement the non-transitory computer-readable medium with instructions stored thereon.

According to an embodiment, the invention provides a computer-implemented system for determining a patient's risk of an adverse drug event based as least on the patient's drug regimen comprising: a database containing two or more of the following data sets related to the patient's risk factors: (1) number of active ingredients in the drug regimen, (2) anticholinergic burden of the active ingredients in the drug regimen, (3) sedative burden of the active ingredients in the drug regimen, (4) QT-interval prolongation risk of the active ingredients in the drug regimen, and (5) competitive inhibition of the active ingredients in the drug regimen; and a calculating module, which applies algorithms to said two or more data sets (e.g., rules that define relationships between said two or more data sets) and calculates a quantitative personalized medication risk score that is representative of the patient's risk for an adverse drug event. A method of using the computer-implemented system may comprise inputting at least one of the data sets (e.g., the number of active ingredients in the drug regimen) into the database. According to an embodiment, the database is pre-programmed to contain data sets relating to the anticholinergic burden, sedative burden, QT-interval prolongation risk and competitive inhibition of various active ingredients, a user inputs the number and identity of the active ingredients from a patient's drug regimen into the database, and the calculating module calculates the quantitative personalized medication risk score based on pre-programmed algorithms as described herein. The calculating module may also use population-based data related to number of active ingredients in a drug regimen, anticholinergic burden, sedative burden, QT-interval prolongation risk and competitive inhibition to provide a population distribution of personalized medication risk scores.

According to an embodiment, the invention provides a method of reducing a risk of an adverse drug event in a patient, wherein the patient has been prescribed a drug regimen that includes at least a first drug and a second drug, the method comprising calculating a quantitative personalized medication risk score that is representative of the patient's risk for an adverse drug event by utilizing one or more embodiments of the methods described herein. According to particular embodiments, the method comprises executing instructions stored on a non-transitory computer-readable medium as described herein (e.g., by using a computing device to execute the instructions).

According to an embodiment, the method comprises combining aggregated risk factor scores representative of each of one or more risk factors, or two or more risk factors, or three or more risk factors, or four or more risk factors, or five or more risk factors associated with the patient's drug regimen in order to calculate the quantitative personalized medication risk score. According to an embodiment, the risk factors are selected from the group consisting of:
1) number of active ingredients in the drug regimen,
2) anticholinergic burden of the drug regimen,
3) sedative burden of the drug regimen,
4) QT-interval prolongation risk of the drug regimen, and
5) competitive inhibition of the drug regimen.

According to an embodiment, the method of reducing a risk of an adverse drug event in a patient further comprises adjusting the patient's drug regimen, based, at least in part, on the quantitative personalized medication risk score, by performing one or more steps of:
(a) removing the first drug and/or the second drug from the patient's drug regimen;
(b) reordering which of the first drug and the second drug is taken first by the patient;
(c) changing the timing of when the first drug and/or the second drug are taken by the patient;
(d) changing time of day when the first drug and/or the second drug are taken by the patient;
(e) replacing the first drug and/or the second drug of the patient's drug regimen with one or more alternate drugs of the same class and/or category as the first drug and/or the second drug;
(f) reducing the dosage of the first drug and/or the second drug from an initial dosage to a reduced dosage;
(g) increasing the dosage of the first drug and/or the second drug from an initial dosage to an increased dosage;
(h) performing a surgical procedure; and adding at least a third drug to the patient's drug regimen.

BRIEF DESCRIPTION OF THE SEVERAL VIEWS OF THE DRAWINGS

The foregoing summary, as well as the following detailed description of embodiments of the invention, will be better understood when read in conjunction with the appended drawings of an exemplary embodiment. It should be understood, however, that the invention is not limited to the precise arrangements and instrumentalities shown.

In the drawings:

FIG. 7 is a table illustrating the weights of each risk factor for the risk scoring system, in accordance with at least one embodiment of the invention.

FIG. 8 is a table illustrating the high-risk groupings of a risk stratification analysis of 320,000 patients, in accordance with at least one embodiment of the invention.

FIG. 10 is a graphic illustrating an example healthcare practitioner's personalized risk mitigation recommendations, in accordance with at least one embodiment of the invention.

DETAILED DESCRIPTION OF THE INVENTION

Figure 1:
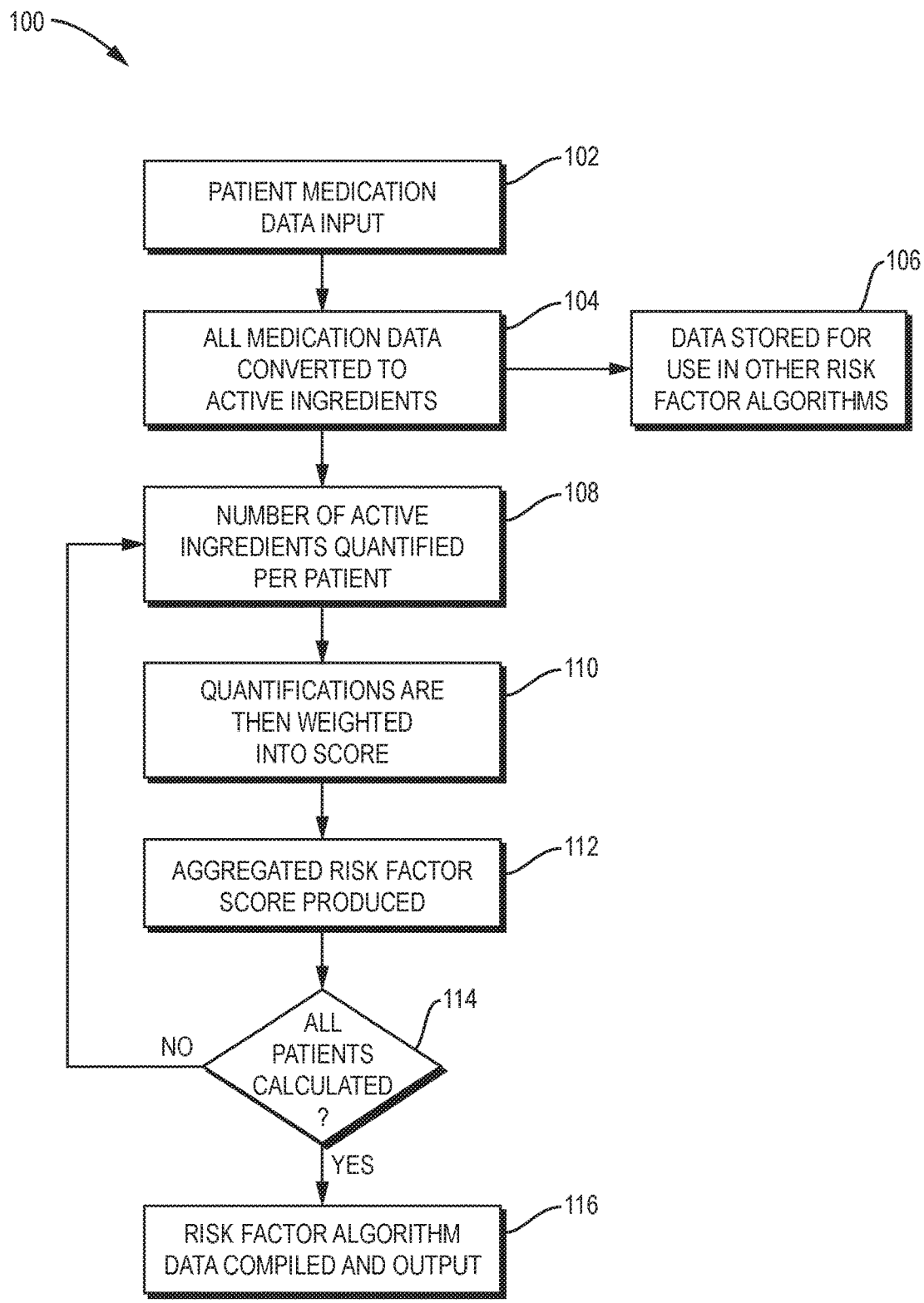
FIG. 1 is a chart illustrating the algorithm used for calculation of risk factor 1, in accordance with at least one embodiment of the invention.

Referring to the drawings in detail, wherein like reference numerals indicate like elements throughout, there is shown in FIGS. 1-17 a system and method for analyzing and presenting patient data, in accordance with an exemplary embodiment of the invention described herein.

History

The Institute of Medicine (IOM) has estimated that 1.5 million preventable Adverse Drug Events (ADEs) occur annually, costing billions of dollars. For older adults in the U.S., there were 99,628 emergency hospitalizations for ADEs in individuals 65 years and older from 2007 to 2009. It has been estimated that 88% of the ADE hospitalizations among older adults are preventable. In a prospective cohort study, 28% of all identified ADEs were ameliorable, meaning that the duration or severity could have been reduced with a different course of action, and 11% were preventable. The ameliorable ADEs were not identified and resolved during clinical care in part due to the physician's lack of response to the ADE. In the primary care setting, ADEs have been shown to occur in 10% to 25% of all adult patients, and at a rate of 50 per 1,000 patient years when specifically evaluating older adults. Medical errors have recently been estimated to result in over 250,000 deaths per year, and medications are known to be a common cause of medical errors associated with harm in primary care. Two common proximal causes of ADEs are lack of knowledge about the medication and lack of knowledge about the patient.

Population stratification systems based on risk adjustment models using different descriptive variables such as demographics, past consumption of health resources or health status have been developed and put in place to offer effective and efficient interventions, to predict cost and outcomes, and to reimburse third party payers.

Several of these models are robust systems from a statistical point of view and have been proven useful in public and private health organizations. The most recent versions of some of these models (ACG-PM or CRGs) combine information about diagnoses, prescriptions, previous costs and use of certain procedures. However, despite their capability to predict a significant portion of the variability in a population's use of health services, they also have significant limitations. First, they rely on the appropriateness of diagnosis coding, but these diagnosis codes are flawed. For example, hierarchies are often imposed, so that a person is coded for only the most severe manifestation among related diseases, meaning the other "lesser" manifestations are ignored for coding purposes. Second, some models use simplified and limited lists of disease codes leading to unrecognized or under reported conditions. Third, the predictive value of these models is directly linked to the timely coding and reporting of patient's condition. Significant lag times (months or even years) can be observed in some claim data files. Fourth, most models do not include information such as life style or socio-economic variables. Fifth, when prescription information is included, drug categories rather than actual drug prescribed and characteristics are used as co-variables. For instance, in one such model, drugs were used as a proxy to define ICD9 codes and to relate the predictive model to disease state. Finally, in all of these models, the consideration for multi-drug interactions and the significant risk of drug-related adverse events is rather absent and omitted.

The IOM has noted that clinical pharmacists play an important role in the reduction of ADEs and other medication-related adverse events. A recent systematic review and meta-analysis evaluating the effect of clinical pharmacists to the healthcare team in the U.S. found that clinical pharmacist interventions and clinical services have a favorable effect on medication safety outcomes including ADEs, adverse drug reactions, medication errors, and hospitalizations due to undesired medication events. Though shown to be an effective resource, clinical pharmacists are expensive to employ, resulting in less than optimal availability in primary care, where it is rare for even a large clinical practice to utilize one pharmacist.

Because health care clinics are comprised of a mixture of healthy patients taking no medications as well as patients with multiple medications and multiple co-morbidities, there is a need for resources and tools that help direct the limited resource of clinical pharmacists to patients at greater risk of experiencing an adverse drug event. Existing tools employed by the EHR primarily use a reminder system, or clinician prompt, when a potential drug interaction, specific medication combination, or patient characteristic might increase the potential for an adverse drug event. It is well known that these system prompts often identify potential issues that are not clinically relevant, and that providers develop "alert fatigue" and routinely ignore these prompts. Physicians and other healthcare providers who prescribe medications primarily interface with these system prompts. Since they are busy delivering care, often times they do not have the time necessary to appropriately provide in-depth evaluation for potential ADEs identified by system prompts. Based on this evidence it's apparent that more accurate tools and clinically meaningful support are needed to optimally reduce adverse drug events in primary care.

There are a few tools that direct the clinical pharmacist to patients with a higher likelihood of drug therapy problems, but these tools are not specifically focused on identifying patients who are more likely to experience an ADE. One tool focuses on assessing the risk of adverse drug reactions in geriatric patients. The tool found that the number of drugs prescribed and a prior history of an adverse drug reaction were the strongest predictors for a subsequent adverse drug reaction. Other variables incorporated into the tool are the presence of four or more comorbid conditions, heart failure, liver disease, or renal failure. Unfortunately, this tool focuses on hospitalized patients and only uses data from the patient's medical record. Furthermore, the tool creates an overall risk score without any detail about specific risks to focus on.

At least some embodiments of the invention described herein fulfill this need for a new population based medication risk stratification and personalized medication risk score using pharmacological characteristics of medication and patient's drug regimen data, such as, but not limited to: (i) number of medications taken; (ii) anticholinergic burden; (iii) sedation burden; (iv) QT prolongation; and (v) competitive inhibition, among others. In some embodiments, by incorporating a plethora of clinical data and through algorithmic development, a software tool has been developed that not only identifies high risk members of the population, but also produces personalized medication risk snapshots which empower health professionals to generate recommendations which mitigate the established risks.

Proof for Number of Medications Being a Risk Factor

Taking multiple medications, known as polypharmacy, can lead to significant increases in health risks and other negative outcomes. It is well known that polypharmacy increases the risk of ADEs in all patients, especially the elderly who typically require more medications. In the United States, older adults use more medications per capita than any other age cohort. Although >50% of all prescription medications are dispensed to persons >60 years, the effects of medications in older adults often are not studied adequately. Furthermore, the frequent use of multiple medications concomitantly is significantly associated with ADEs among older adults. As the proportion of Americans aged >60 years increases rapidly, the incidence of ADEs among older adults will increase exponentially. This is a major public health problem in terms of economic, clinical, and humanistic outcomes for our nation's most vulnerable population. Another study has indicated that polypharmacy was associated with injurious falls as well as increased numbers of injurious falls in middle-age to older adults. Further studies showed that drug-drug interaction risks increase in association with the number of medications being taking. This evidence as well as the abundance of other evidence not specifically mentioned signified the necessary inclusion of the number of medications as a risk factor for stratifying patient health risks.

In some embodiments, a score for risk factor 1 (i.e., number of active ingredients risk score) may be greater than 0, or 1, or 3, or 6, or 9. In some embodiments, a score for risk factor 1 (i.e., number of active ingredients risk score) may be about 0, or 1, or 3, or 6, or 9, or 12. In some embodiments, a score for risk factor 1 (i.e., number of active ingredients risk score) may be less than or equal to 1, or 3, or 6, or 9, or 12. In some embodiments, a score for risk factor 1 that may be associated with a high risk for an adverse drug interaction may be a score for risk factor 1 of 6, or 9, or 12; or a score for risk factor 1 that is greater than 3.

Proof for Anticholinergic Burden Being a Risk Factor

The anticholinergic activity expressed by a drug is directly related to its potential to bind to muscarinic acetylcholine (mACh) receptors. This binding prohibits the usual binding of naturally occurring acetylcholine, creating anticholinergic toxicities. According to clinical and laboratory observations, this blockade of cholinergic transmission lead to the development of both acute and chronic cognitive impairment. As a result of this mACh receptor activity, anticholinergic medications have adverse effects affecting both central and peripheral nervous systems.

Medications with anticholinergic (ACH) activity are frequently prescribed for common conditions that affect older adults, such as depression, insomnia, pain, and urinary incontinence. Different pharmacologic classes of ACH medications have varying degrees of ACH activity. Providers caring for older adults tend to be well aware of the strong ACH activity of medications such as bladder antispasmodics and tricyclic antidepressants but not necessarily aware of the relatively strong ACH activity of certain antidepressants and antipsychotics. They also may not be aware of the weak ACH activity of some commonly prescribed medications for older adults, such as antihypertensives and diuretics. More importantly, providers may not realize that using multiple medications with weaker ACH activity concomitantly can have additive effects.

As mentioned previously, anticholinergic medications affect both the central and peripheral nervous systems. These adverse effects may include: dry mouth, dry eyes, blurred vision, constipation, urinary retention, worsening angina, cardiac dysrhythmias, agitation, confusion, and delirium. Accumulating evidence suggests that ACH medications, especially cumulative ACH exposure, may also contribute to chronic functional decline and impairments in daily functioning, including cognitive deficits, memory impairment, fatigue, weakness, gait instability, as well as an increased incidence of dementia, falls, hospitalizations, and all-cause mortality.

Although cognitive and functional decline occur frequently in older adults, medications as a contributing factor may be overlooked in the traditional health care model, which focuses on diagnosis and treatment of diseases by prescribing additional medications, some of which could be inappropriate or further damaging. For example, agitation from ACH medication-induced constipation may be mistakenly treated with antipsychotics, further contributing to ACH adverse effects. In summary, ACH medications can affect cognitive and physical function in older adults considerably and providers may not attribute these adverse effects to cumulative ACH exposure.

In some embodiments, a score for risk factor 2 (i.e., cognitive impairment risk score) may be greater than 0, or 1, or 2, or 3, or 4, or 5. In some embodiments, a score for risk factor 2 (i.e., cognitive impairment risk score) may be about 0, or 1, or 2, or 3, or 4, or 5, or 6. In some embodiments, a score for risk factor 2 (i.e., cognitive impairment risk score) may be less than 1 or equal to 2, or 3, or 4, or 5, or 6. In some embodiments, a score for risk factor 2 that may be associated with a high risk for an adverse drug interaction may be a score for risk factor 2 of 4, or 5, or 6; or a score for risk factor 2 that is greater than 3.

Proof for Sedation Burden Being a Risk Factor

Sedation is mediated by multiple mechanisms in the central nervous system (CNS) and differs by medication class based on their physiological mechanisms of action. The following are all proposed sedation mechanisms and their associated medication classes:

Agonism of the benzodiazepine receptor in the GABA-A complex—benzodiazepines & barbiturates, muscle relaxants Antagonism of histamine H1 receptors in the CNS—first generation antihistamines, antipsychotics, second generation antidepressants, and tricyclic antidepressants Binding to the µ-opioid receptor—opioids Antagonism of alpha-1-adrenergic receptors in the CNS—antipsychotics Antagonism alpha-2-adrenergic receptors in the CNS—mianserin Medications with sedative (SDV) activity are frequently prescribed for common conditions that affect older adults, such as insomnia and pain, and different classes of SDV medications have varying degrees of SDV activity. Providers caring for older adults tend to be well aware of the strong SDV activity of medications such as benzodiazepines and opioids but they may not be aware of the weak SDV activity of some commonly prescribed medications for older adults, such as certain antidepressants and antipsychotics. Further, providers may not realize that using multiple medications with weaker SDV activity concomitantly can have additive effects.

Sedative load refers to cumulative exposure to medications with SDV properties. Models that take into account use of multiple medications are important because older adults often use multiple SDV medications and cumulative SDV load has been associated with various ADEs. Regarding the latter, these include cognitive decline, physical impairment, and increased risk of death.

In some embodiments, a score for risk factor 3 (i.e., sedation risk score) may be greater than 0, or 1, or 2, or 3, or 4. In some embodiments, a score for risk factor 3 (i.e., sedation risk score) may be about 0, or 1, or 2, or 3, or 4, or 5. In some embodiments, a score for risk factor 3 (i.e., sedation risk score) may be less than or equal to 1, or 2, or 3, or 4, or 5. In some embodiments, a score for risk factor 3 that may be associated with a high risk for an adverse drug interaction may be a score for risk factor 3 of 4 or 5; or a score for risk factor 3 that is greater than 3.

Proof for QT Prolongation Being a Risk Factor

Prolongation of the QT interval may predispose patients to syncopal events and a particular polymorphic ventricular tachycardia described as Torsade de Pointes (TdP), which may lead to sudden death. This progression is more common with long episodes of TdP, but it has also been related to QTc interval length. It has been estimated that each 10 msec increase in QTc corresponds to a 5-7% exponential increase in risk for TdP. In general, TdP is rare when QTc is <500ms, accounting for less than 10% of all cases. Several studies have shown a positive correlation between increased QTc length and mortality, reinforcing the need to take action when a prolonged QTc is identified. Specifically, results have shown that the QTc interval length was a significant predictor of mortality with a hazard ratio of 1.13 (1.12-1.14, p<0.001), meaning patients with a prolonged QTc interval are 13% more likely to experience death than those with a normal QTc interval length.

The reality is that patients take many medications and have individual risk factors that may predispose or protect them from QT prolongation and TdP. Risk factors for TdP include: age, female gender, abnormal heart rhythm, slow heart rate, hypokalemia, hypomagnesemia, use of certain diuretics, use of antiarrhythmic medications (especially Class IA, IC, and III), use of QT-prolonging drugs along with drug-drug interactions, and QTc interval. Not all of these factors contribute equally to risk of TdP, but they should all be accounted for whenever the information is available.

The frequency of QT prolongation leading to Torsade de Pointes in community-dwelling older adults is not well characterized. It has been estimated that >400,000 lives are lost to sudden cardiac death annually. Roughly 10-20% of these individuals have no evidence of structural heart disease. It has also been shown that the incidence of sudden cardiac death increases with age, such that the annual incidence for 50-year-old men is ~100 per 100,000 population, compared with 800 per 100,000 for 75-year-old men.

In the past 25 years, 30 drugs have been removed from the market, the majority (56%; n=17) of which were removed due to various cardiac safety issues. Seven of the above-mentioned medications were removed from the U.S. market due to QT-prolongation, including: terodiline, terfenadine, astemizole, grepafloxacin, cisapride, and ondansetron (32 mg, intravenously). That makes up 23% of the last 30 medications removed. Many of these medications are metabolized via the CYP450 enzymatic system and would likely be subjected to drug-drug interactions in our elderly patients with multiple medications. Such relationship has been established for QT prolonging drugs such as triamterene, indapamide, erythromycin, cisapride, diphenhydramine, thioridazine, droperidol, sildenafil, domperidone, pimozide, risperidone, olanzapine, bupropion, and rosuvastatin. It has been estimated that roughly 35% of patients experiencing TdP from non-cardiac drugs had a potential metabolic interaction.

In some embodiments, a score for risk factor 4 (i.e., LQTS risk score) may be greater than 0, or 2, or 5, or 7. In some embodiments, a score for risk factor 4 (i.e., LQTS risk score) may be about 0, or 2, or 5, or 7, or 10. In some embodiments, a score for risk factor 4 (i.e., LQTS risk score) may be less than or equal to 2, or 5, or 7, or 10. In some embodiments, a score for risk factor 4 that may be associated with a high risk for an adverse drug interaction may be a score for risk factor 4 of 7 or 10; or a score for risk factor 4 that is greater than 5.

Proof for Competitive Inhibition Being a Risk Factor

To understand why older adults are highly susceptible to ADEs and why they respond differently to medications, it is necessary to consider the relationship between the metabolism of a particular medication and its observed clinical effect. In brief, the clinical effect of a medication is dependent on: (1) its systemic concentration and (2) its concentration at the target site. Co-administration of multiple medications and, hence, multi-drug interactions (DDIs) can significantly influence medication concentrations. The initial steps in the metabolism of a medication are mostly mediated by the cytochrome P450 (CYP) enzyme family. Most DDIs involve the CYP450 system. Each CYP450 enzyme has selective substrates, inhibitors, and inducers of its activity. Inducers and inhibitors are medications that either increase or decrease the activity of a particular CYP450 enzyme. A medication is a substrate of a CYP450 enzyme if this particular enzyme can transform the medication into a metabolite. A substrate can also act as an inhibitor by competing with other co-administered substrates for binding to the same enzyme (i.e., competitive inhibition). The substrate with the greatest affinity for the enzyme will always inhibit those with lesser affinity. When multiple medications have the same affinity for a particular enzyme, the substrate with the highest dose will always inhibit those with a lower dose. As a consequence, medications can increase or decrease enzyme activity, which can lead to higher or lower systemic concentrations of the medication and/or co-administered medications. Through the mechanism of competitive inhibition, DDIs can profoundly affect medication response in older adults. The invention described herein incorporates pharmacokinetic drug properties, e.g., enzyme affinity coefficients, to identify competitive inhibition whenever multiple medications are used concomitantly.

Although DDIs are widely recognized as a major cause of ADEs among older adults, the ever-increasing number of medications on the market as well as the increasing number of medications simultaneously consumed by older adults have made the determination of the exact prevalence of DDIs in this population challenging. Clinical evidence shows that the risk of a DDI was 50% when a patient takes 5 to 9 medications, 81% when taking 10 to 14, 92% when taking 15 to 19, and 100% when a patient is taking 20 or more medications. Even further, the addition of each medication to a 5-medication regimen increased the risk of a potential CYP-mediated DDI by 12%. It is an unfortunate reality that more and more of the global population are taking higher amounts of medications, especially as they age. In a sample of 1,143 patients 60 years or older, researchers detected a total of 1,053 potentially major or substantial drug interactions among 501 patients. Each patient had, on average, 2.1 major or substantial interactions, with DDIs accounting for 66.1%. Further, the pharmacologic classes most frequently involved in major interactions included some of the most commonly used medications by older adults, specifically beta-blockers (15.6% of interactions), antidepressants (13.0%), antiplatelets (10.1%), opioids (9.9%), and anti-inflammatory agents (7.6%).

In some embodiments, a score for risk factor 5 (i.e., competitive inhibition risk score) may be greater than 0, or 1, or 2, or 3, or 4, or 5, or 6, or 7, or 8, or 9, or 10, or 11, or 12, or 13, or 14, or 15, or 16, or 17, or 18, or 19. In some embodiments, a score for risk factor 5 (i.e., competitive inhibition risk score) may be about 0, or 1, or 2, or 3, or 4, or 5, or 6, or 7, or 8, or 9, or 10, or 11, or 12, or 13, or 14, or 15, or 16, or 17, or 18, or 19, or 20. In some embodiments, a score for risk factor 5 (i.e., competitive inhibition risk score) may be less than or equal to 1, or 2, or 3, or 4, or 5, or 6, or 7, or 8, or 9, or 10, or 11, or 12, or 13, or 14, or 15, or 16, or 17, or 18, or 19, or 20. In some embodiments, a score for risk factor 5 that may be associated with a high risk for an adverse drug interaction may be a score for risk factor 5 of 7, or 8, or 9, or 10, or 11, or 12, or 13, or 14, or 15, or 16, or 17, or 18, or 19, or 20; or a score for risk factor 5 that is greater than 6.

In addition to competitive inhibition- and DDI-influenced variation in medication response in older adults, genetic variation can also result in altered medication response.

Pharmacogenomic (PGx) testing can provide insight into how an individual may response to a certain medication. Genetic variation in drug-metabolizing enzymes and drug transporters can significantly affect medication concentrations and thus may put individuals at risk for toxicity or ineffectiveness. Many enzymes involved in drug metabolism are highly polymorphic resulting in their activity being increased or decreased. Such variation can lead to lower or higher concentrations of a medication and/or its metabolites during medication metabolism. For example, the CYP2D6 enzyme is known to be involved in the metabolism of many psychiatric medications and several opioids. This enzyme has been found to exhibit high individual variability in metabolism mainly caused by genetic variations. As a result of the genetic variations, patients can display an increased sensitivity or decreased therapeutic effect to psychiatric or opioid medications, depending on their personal genetic variance.

Unlike traditional DDI software programs, which provide information on only two-medication combinations at a time and do not take into account PGx, pharmacokinetic, and pharmacodynamic principles, the invention described herein assesses multi-drug combinations in the presence of possible PGx variations simultaneously. This unique approach for assessment affords a much stronger application to patients, particularly older adults, with chronic medical conditions and polypharmacy.

Methods for Determining Medication Risk Stratification and Preparation of a Personalized Medication Risk Score In some embodiments, there are provided methods for analyzing pharmacological characteristics of medication and patient's drug regimen data to generate new population based medication risk stratification and a personalized medication risk score. Exemplary embodiments of these methods are described in FIGS. 1-6, below.

FIG. 1 is a method 100 for calculating an aggregated risk-factor score representative of the number of medications taken by a patient (also referred to herein as "risk factor 1"), in accordance with at least one embodiment of the invention.

At step 102, patient medication data may be input into, or received by, a computer or a computer processor. Medication data may include patient identification codes identifying specific patients as well as, but not limited to, regimen-level medication profiles encoded using National Drug Codes (NDCs) or the NIMH's RxNorm RXCUI identifiers to identify medication products.

At step 104, the patient medication data may be converted to active ingredients data. As used herein, the term active ingredients may refer to the biologically active chemical(s) contained within medication products. In this embodiment, active ingredient data is encoded as text. Further, the conversion of medication data described above to active ingredient data is performed by the application of a mapping of NDC data and RXCUI data to their active ingredients specifically developed for this invention.

At step 106, the active ingredients data and/or the patient medication data may be stored in a data storage unit.

At step 108, the number of active ingredients may be quantified per patient. This quantification of active ingredient(s) occurs through the application of a string-count algorithm. Initially, distinct active ingredients per patient are filtered. Then, the number of distinct active ingredients per patient is counted. Lastly, the number of unique active ingredients for that patient is outputted. (As described herein, according to an alternative embodiment, at step 108, the risk of one or more side effects for each active ingredient may be quantified per patient, e.g., by utilizing data from the FDA Adverse Event Reporting System, and the quantified risk of side effect(s) for that patient is outputted.)

At steps 110 and 112, the quantified number of active ingredients (or quantified risk of one or more side effects associated with the active ingredients) may be weighted and analyzed to produce the aggregated risk factor score. The aggregated risk factor score of active ingredient count may refer to the clinically relevant indication of medication ingestion risk. In some embodiments, the aggregated risk factor score may be calculated by analyzing active ingredients for clinical relevance. In some embodiments, to perform this analysis, active ingredient data may be mapped to each ingredient's ability to reach medically-relevant physiologic systemic circulation. Multiple factors may be used into this analysis, including but not limited to, route of administration and chemical characteristics of each active ingredient. The active ingredients determined to be medically relevant are then quantified and weighted into the aggregated risk factor score through a numeric transformation algorithm.

At step 114, a determination of whether all patients' aggregated risk factor scores have been calculated may be made. This step may confirm that all patients contained within the analyzed patient regimen data were considered and analyzed. This step can ensure the quality as well as reliability of the inventions' score outputs.

In response to a determination that all patients' aggregated scores have not been calculated (i.e., "No"), the method 100 may revert back to step 108.

In response to a determination that all patients' aggregated scores have been calculated (i.e., "Yes"), the method 100 may proceed to step 116.

At step 116, the risk factor algorithm data may be compiled and output. Data compilation may include joining the aggregated risk factor score to medication regimen for each patient identification code. The joining of the aggregated risk factor score to medication regimen for each patient identification code may be referred to as the active ingredient risk factor algorithm data for this particular risk factor. In some embodiments, the active ingredient risk factor algorithm data includes a list of patient identification codes and their associated aggregated risk factor score based on the number of the active ingredients in their regimen.

Figure 2:
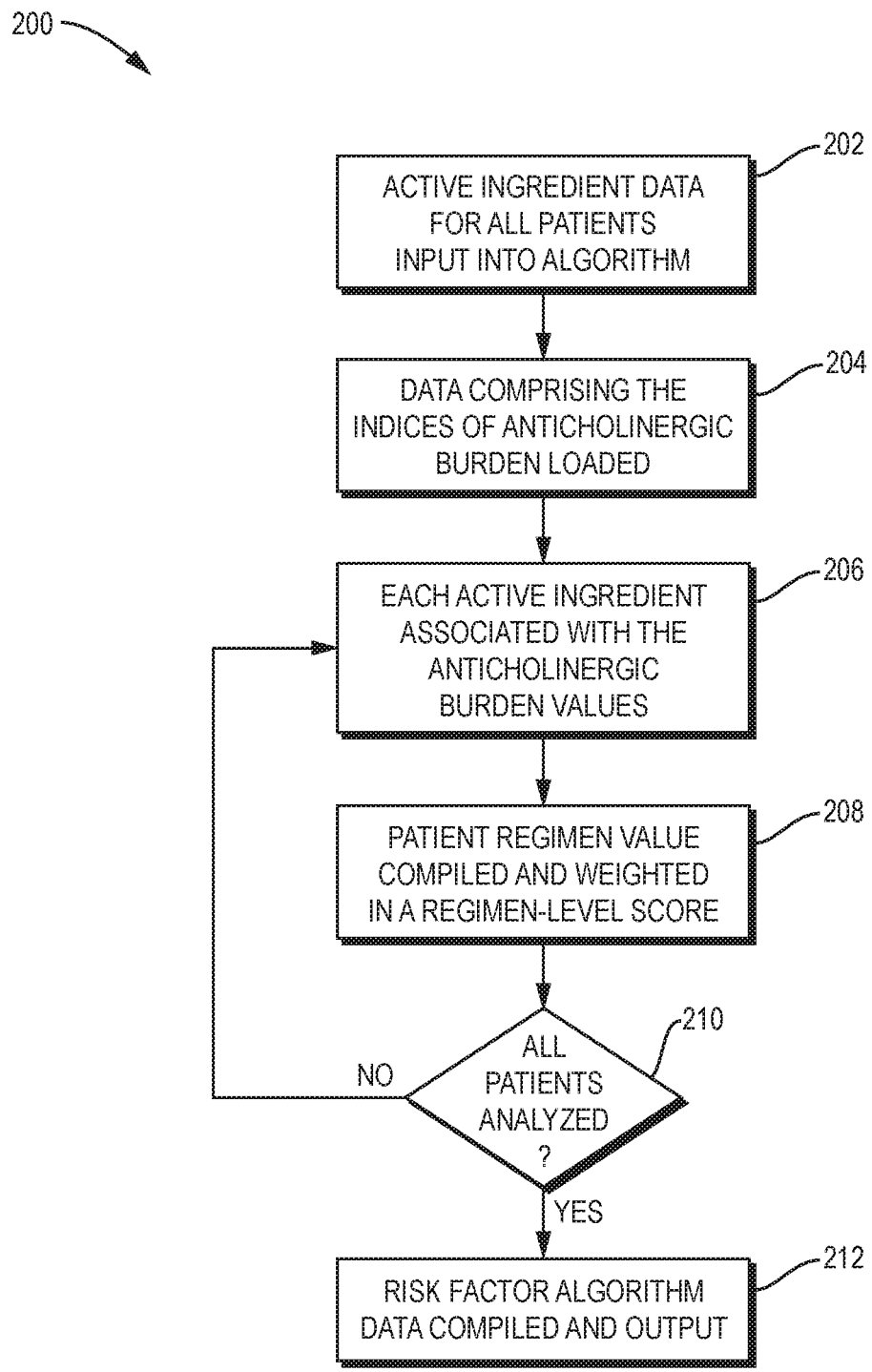
FIG. 2 is a method illustrating the algorithm used for calculation of risk factor 2, in accordance with at least one embodiment of the invention.

FIG. 2 is a method 200 for calculating data representative of anticholinergic burden (also referred to herein as "risk factor 2"), in accordance with at least one embodiment of the invention.

At step 202, active ingredient data may be input into, or received by, the computer or the computer processor.

At step 204, anticholinergic burden indicia data may be loaded into, or received by, the computer or the computer processor. Anticholinergic burden indicia data may refer to the propensity some medications have to negative interactions with the central and peripheral nervous system's cholinergic activity. Quantitative values have been assigned to medications which display such negative interaction activity. A dataset containing each active ingredient and a quantitative value ranging from 0 to 3 to indicate the anticholinergic activity is utilized to calculate the anticholinergic burden indicia data.

At step 206, each active ingredient may be associated anticholinergic burden values. In some embodiments, each active ingredient may be associated anticholinergic burden values by first importing the active ingredient data of each patient regimen. The active ingredient data is then joined with the anticholinergic indicia data to relate each regimen active ingredient to a quantitative anticholinergic activity value.

At step 208, patient regimen values may be compiled and weighted to produce a aggregated regimen-level anticholinergic score. Initially, the associated active ingredient data and anticholinergic burden values may be compiled into an aggregated regimen-level anticholinergic value using a summed process. The regimen-level anticholinergic risk factor values may be weighted into a clinically relevant, regimen-level anticholinergic risk factor score through a numeric transformation algorithm. This weighting can be important for distinguishing the overall sum of anticholinergic activity due to a patient's regimen, i.e. risk factor value, to a score that is relevant for population stratification as well as clinician intervention.

At step 210, a determination of whether all patients' aggregated regimen-level anticholinergic risk factor scores have been calculated may be made. The aggregated regimen-level anticholinergic risk factor algorithm may confirm that all patients contained within the patient regimen data were considered and analyzed in order to ensure the quality as well as reliability of the score outputs.

In response to a determination that all patients' aggregated scores have not been calculated (i.e., "No"), the method 200 may revert back to step 206.

In response to a determination that all patients' aggregated scores have been calculated (i.e., "Yes"), the method 200 may proceed to step 212.

At step 212, the regimen-level anticholinergic risk factor algorithm data may be compiled and output. The data compilation refers to the joining of the final regimen-level anticholinergic risk factor score of each patient to each patient identification code. The output of this compilation is referred to as the anticholinergic burden risk factor algorithm data for this particular risk factor. Specifically, this data is a list of patient identification codes and their associated aggregated regimen-level anticholinergic burden risk factor score based on the anticholinergic activity of their regimen.

Figure 3:
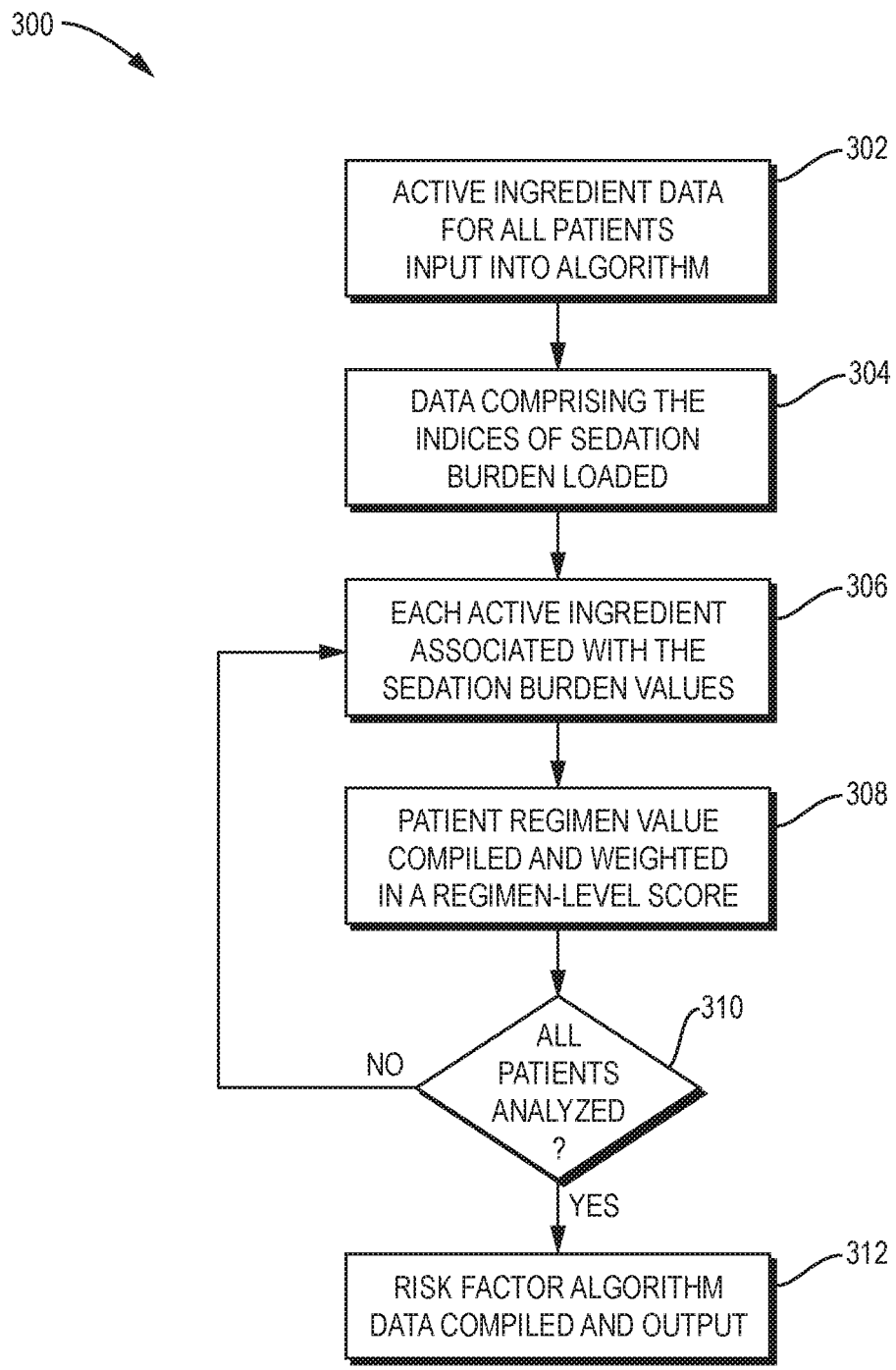
FIG. 3 is a chart illustrating the algorithm used for calculation of risk factor 3, in accordance with at least one embodiment of the invention.

FIG. 3 is a method 300 for calculating data representative of sedative burden (also referred to herein as "risk factor 3"), in accordance with at least one embodiment of the invention. There are multiple known mechanisms through which medications can cause negative sedative side-effects. Accounting for these sedative side-effects can improve population stratification.

At step 302, active ingredient data may be input into, or received by, the computer or the computer processor.

At step 304, sedative burden indicia data may be loaded into, or received by, the computer or the computer processor. For example, each active ingredient can be associated to their propensity to cause sedation. Active ingredients may be given a numeric value between 0 and 3 based on the degree of their propensity to have sedative side-effects, and the results were compiled into a table referred to as the sedative burden indicia data.

At step 306, each active ingredient may be associated sedative burden values. Each active ingredient can be associated to their propensity to cause sedation. The active ingredient data is then systematically joined with the sedative indicia data to relate each regimen active ingredient to a quantitative sedation burden value.

At step 308, patient regimen values may be compiled and weighted to produce a regimen-level score. The quantitative sedation burden values may be compiled into separate regimen-level sedative risk factor value using a summed processing. Following the compilation of regimen-level sedative risk factor values, the regimen-level sedative risk factor values may be weighted into a clinically relevant sedative burden regimen-level score through a numeric transformation algorithm. This weighting can distinguish the overall sum of sedation activity due to a patient's regimen risk factor value, to a score that is relevant for population stratification as well as for clinician intervention.

At step 310, a determination of whether all patients' aggregated risk factor scores have been calculated may be made. The aggregated sedative burden regimen-level risk factor algorithm may confirm that all patients contained within the patient regimen data were considered and analyzed in order to ensure the quality as well as reliability of the score outputs.

In response to a determination that all patients' aggregated scores have not been calculated (i.e., "No"), the method 300 may revert back to step 306.

In response to a determination that all patients' aggregated scores have been calculated (i.e., "Yes"), the method 300 may proceed to step 312.

At step 312, the regimen-level sedative burden risk factor algorithm data may be compiled and output. The data compilation refers to the joining of the final regimen-level sedative burden risk factor score of each patient to each patient identification code. The output of this compilation is referred to as the regimen-level sedative burden risk factor algorithm data for this particular risk factor. Specifically, this data is a list of patient identification codes and their associated aggregated regimen-level sedative burden risk factor score based on the sedative effects of their regimen.

Figure 4:
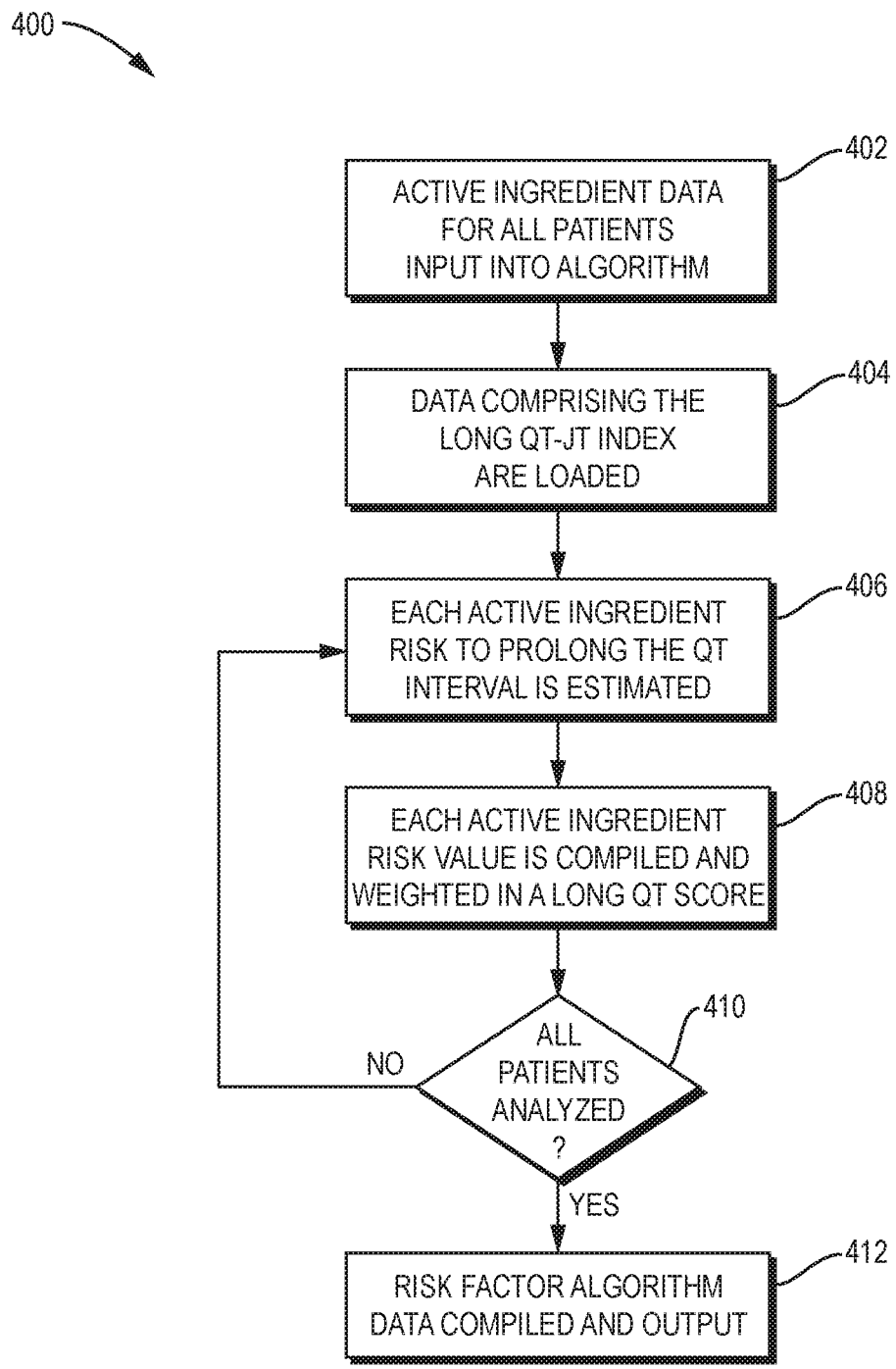
FIG. 4 is a chart illustrating the algorithm used for calculation of risk factor 4, in accordance with at least one embodiment of the invention.

FIG. 4 is a method 400 for calculating data representative of Long-QT syndrome. At least some embodiments for calculating Long-QT scores are described in the '707 application and the '555 application. The Long QT-JT index estimates, in a quantitative manner, the risk of a specific active ingredient to prolong the QT interval. The Long QT-JT score takes into account various risk factors, including gender, age, the concomitant administration of diuretics, beta-blockers, Class IA or Class III antiarrhythmics, potassium and magnesium blood levels, the concomitant administration of QT prolonging drugs (Long QT-JT index) and the risk of drug-drug interactions to estimate the clinical risk for a patient to experience torsades de pointes. Various algorithms generate a risk score which is compiled and included in the algorithms used to calculate the inventions' score outputs.

At step 402, active ingredient data may be input into, or received by, the computer or computer processor.

At step 404, Long QT-JT index data may be loaded into, or received by, the computer or the computer processor.

At step 406, each active ingredient risk to prolong the QT interval is estimated.

At step 408, each active ingredient risk value is compiled and weighted in a long QT score.

At step 410, a determination of whether all patients' long QT scores have been calculated may be made.

In response to a determination that all patients' long QT scores have not been calculated (i.e., "No"), the method 400 may revert back to step 406.

In response to a determination that all patients' long QT scores have been calculated (i.e., "Yes"), the method 400 may proceed to step 412.

At step 412, the Long QT risk factor algorithm data may be compiled and output.

Figure 5:
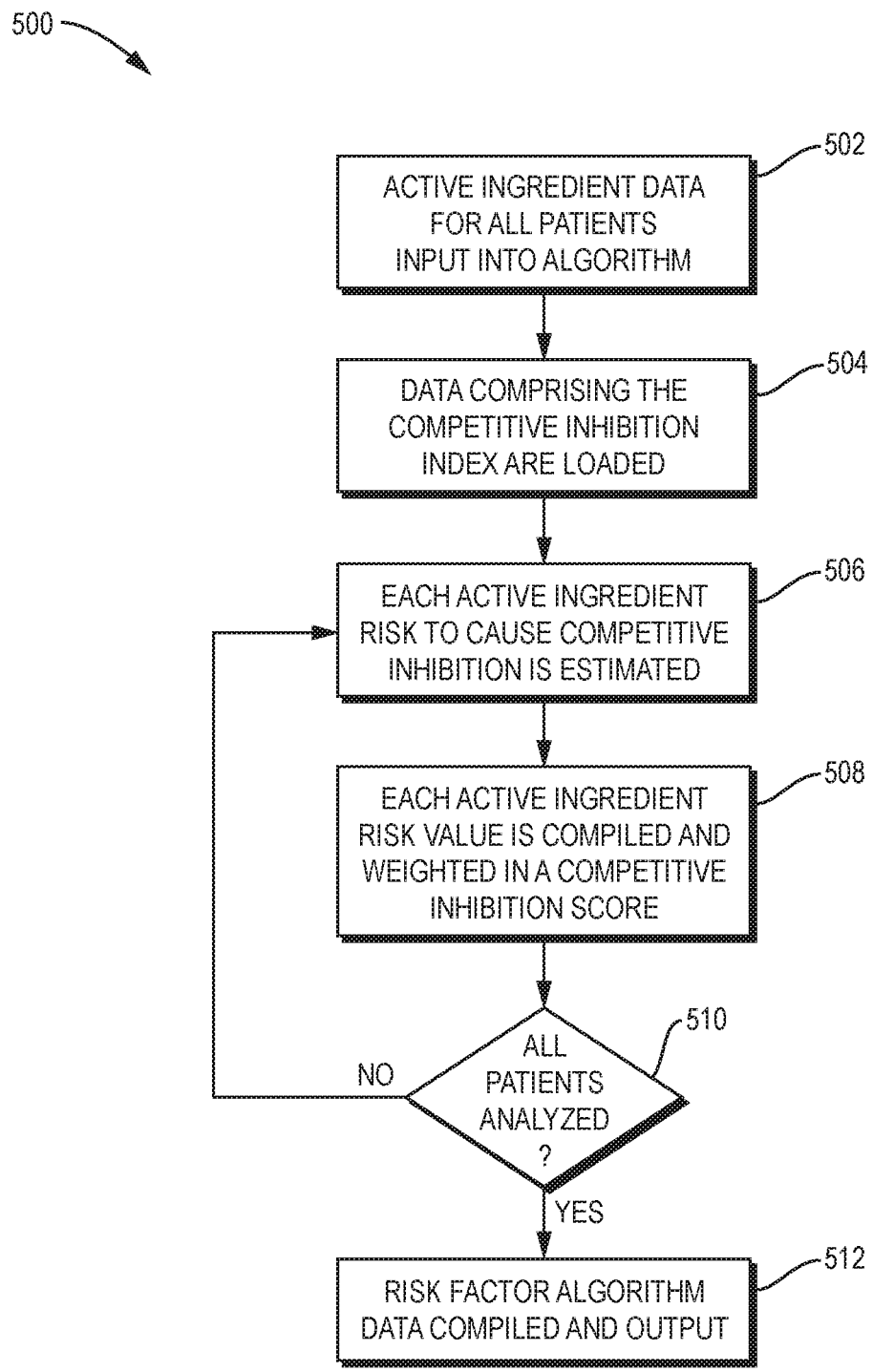
FIG. 5 is a chart illustrating the algorithm used for calculation of risk factor 5, in accordance with at least one embodiment of the invention.

FIG. 5 is a method 500 for calculating data representative of competitive inhibition. At least some embodiments of methods used to identify, predict and manage multi-drug interactions due to competitive inhibition are described in the '704 application and the '539 application. These conditions are recognized by algorithms developed in the context of embodiments of the invention described herein to generate a competitive inhibition risk score. This risk score in compiled and included in the algorithm used to calculate the inventions' score output.

At step 502, active ingredient data may be input into, or received by, the computer or computer processor.

At step 504, competitive inhibition index data may be loaded into, or received by, the computer or the computer processor.

At step 506, each active ingredient risk to cause competitive inhibition is estimated.

At step 508, each active ingredient risk value is compiled and weighted in a competitive inhibition score.

At step 510, a determination of whether all patients' competitive inhibition scores have been calculated may be made.

In response to a determination that all patients' competitive inhibition scores have not been calculated (i.e., "No"), the method 500 may revert back to step 506.

In response to a determination that all patients' competitive inhibition scores have been calculated (i.e., "Yes"), the method 500 may proceed to step 512.

At step 512, the competitive inhibition risk factor algorithm data may be compiled and output.

Figure 6:
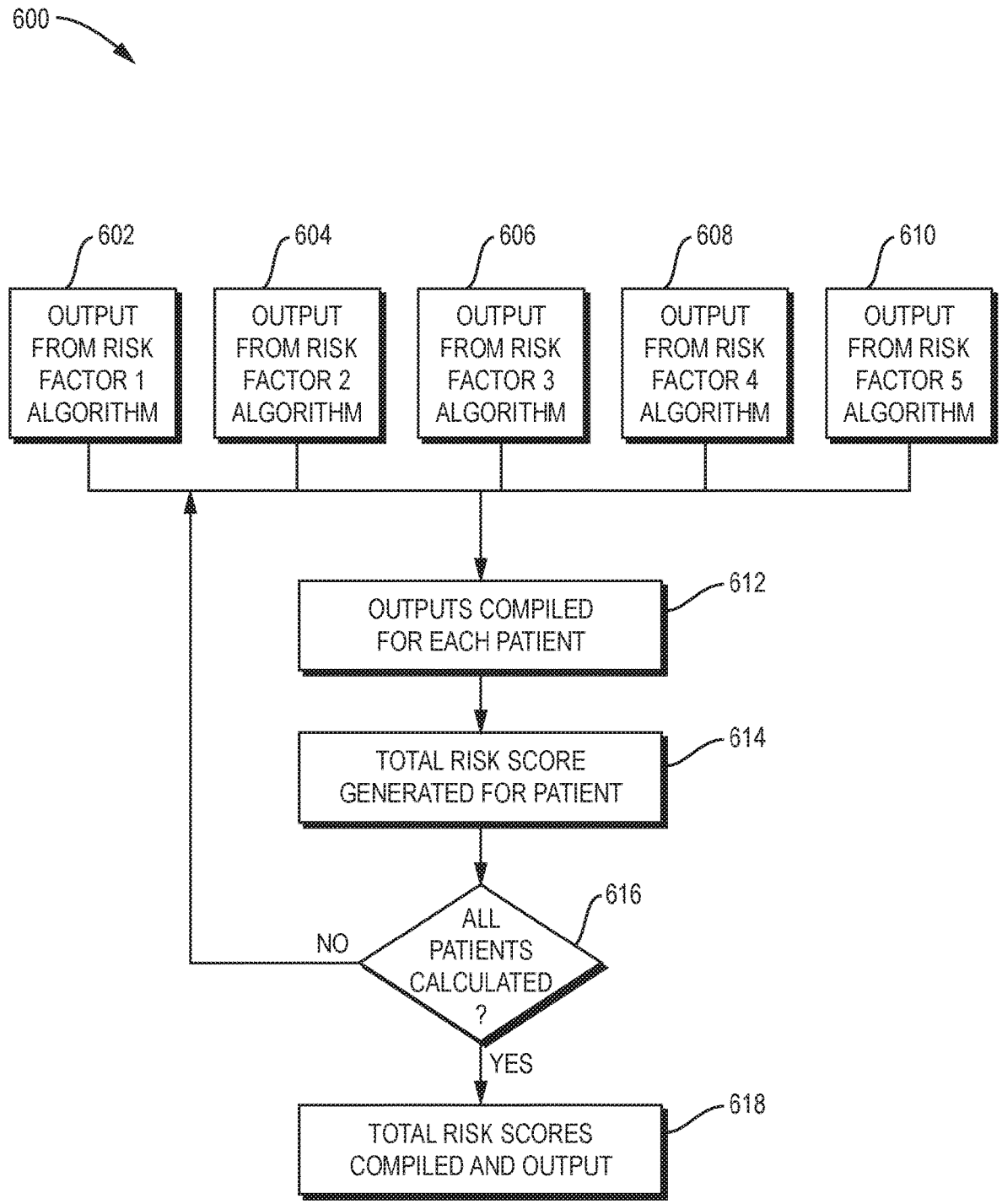
FIG. 6 is a graphic illustrating the primary equation used to calculate the total risk score, in accordance with at least one embodiment of the invention.

FIG. 6 is a method 600 for analyzing pharmacological characteristics of medication and patient's drug regimen data to generate new population based medication risk stratification and a personalized medication risk score, in accordance with at least one embodiment of the invention.

At step 602, data representative of the number of medications taken for one or more patients (as calculated using method 100) may be input into, or received by, the computer or the computer processor.

At step 604, data representative of the anticholinergic burden for one or more patients (as calculated using method 200) may be input into, or received by, the computer or the computer processor.

At step 606, data representative of the sedative burden for one or more patients, may be input into, or received by, the computer or the computer processor.

At step 608, data representative of QT prolongation for one or more patients (as calculated using method 400) may be input into, or received by, the computer or the computer processor.

At step 610, data representative of competitive inhibition for one or more patients (as calculated using method 500) may be input into, or received by, the computer or the computer processor.

At step 612, each of the data may be compiled for each patient. Due to each risk factor algorithm data containing the same patient identification code, the aggregated risk factor score data generated by each risk factor algorithm is able to be compiled. To perform this compilation, each aggregated risk factor score is joined to a data frame where the patient identification code is the same. The result of this is a data frame with a patient identification code along with each risk factor algorithm score for that patient.

At step 614, a total risk score may be generated for each patient. Upon the output of a dataset containing a patient identification code and their aggregated risk factor scores for all risk factors, a summed processing is applied. The resulting output contains a patient identification code, the aggregated score of each risk factor, as well as the patient's total risk score. The total risk score, based on the various risk factor scores, indicates the overall risk of a patient's regimen to the health of that patient.

At step 616, a determination of whether all patients' total risk scores have been calculated may be made. It is of the greatest importance to ensure that the total risk score algorithm confirms that all patients contained within the patient regimen data were compiled and analyzed in order to ensure the quality as well as reliability of the inventions' score outputs.

In response to a determination that all patients' total risk scores have not been calculated (i.e., "No"), the method 600 may revert back to step 602.

In response to a determination that all patients' total risk scores have been calculated (i.e., "Yes"), the method 600 may proceed to step 618.

At step 618, the total risk scores for all patients may be compiled and output. Once all patient risk factor and total risk scores are calculated, the individual data are all compiled into one data table. The resulting compiled dataset is a list of all patient identification codes, their associated aggregated risk factor scores, as well as their total risk score.

Explanation of Underlying Algorithm That Combines All Risk Factors

Following the calculation of each risk factor's value using their respective algorithm as summarized herein, in method 600, two final algorithms may be applied in order to generate a complete risk perspective. The first algorithm may involve taking the value output from each of the individual risk factor algorithms directly relating to the medications identified in the patient regimen. Following this output, the algorithm may convert each risk factor value into a score designed to properly weight each factor into a clinically relevant score. Following the conversion of all risk factor values to scores, a final algorithm may be applied to combine the individual risk factor scores to reflect a cumulative patient risk score. An example of the algorithm that relates all individual risk factor values into distinct, weighted scores is summarized in FIG. 7. This cumulative score, referred to as the Personalized Medication Risk Score, is indicative of the overall health risks a patient's medication regimen imposes. In summary, each risk factor algorithm may be simulated over the provided medication data for every patient within the data set, the resulting risk factor values may be converted to risk factor score by another algorithm, and then a final algorithm may combine all scores into a cumulative total risk score.

Risk Factor High-Risk Thresholds

In order to find high risk members within a patient population, score thresholds indicating high risk needed to be created. The accuracy of these score thresholds, depicted in FIG. 8, to capture high risk members of a population can be of vital importance for both stratifying the risks of a population as well as mitigating those risks quickly and effectively. The score thresholds that indicate a high risk for each risk factor were determined through a multi-step process, as well as clinical validation of the results. The multi-step process began with a literature review of peer-reviewed data. Once the data was analyzed for preliminary baselines, sample outputs of the risk stratification tool were used to determine the percentage of members, for various healthcare populations, the high risk thresholds captured. Finally, expenditure data for a large cohort of patients were analyzed and the risk scores were compared to their yearly median expenditure. Using these data, there is a high confidence that the high-risk thresholds designated are accurately capturing the portions of the patients who are at risk for medication-related problems as well as higher healthcare utilization costs.

Visualization of Results

Figure 9:
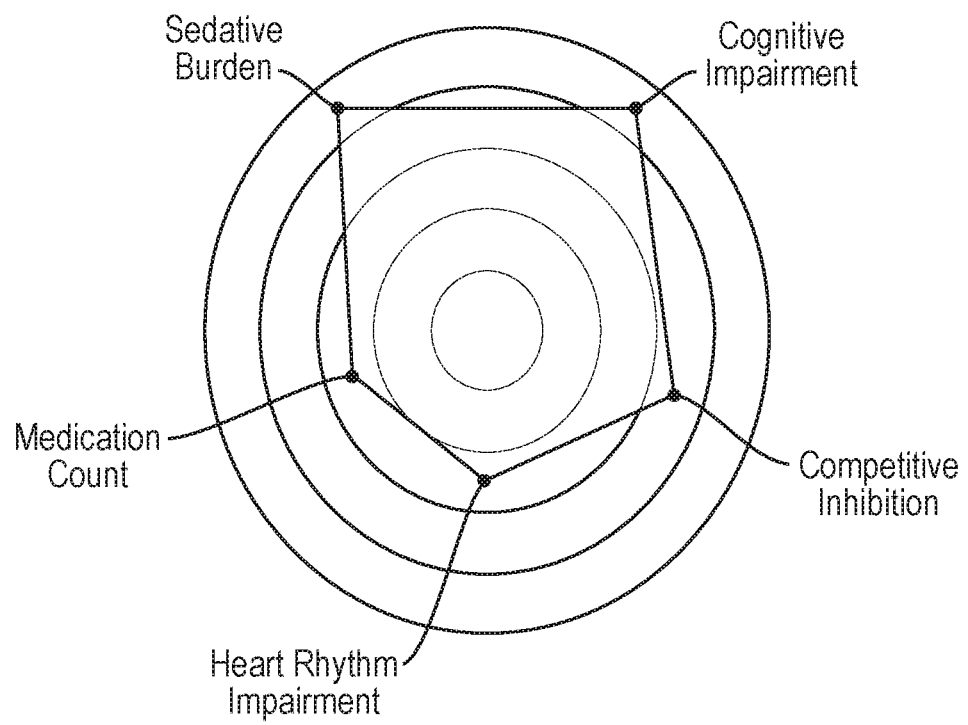
FIG. 9 is the depiction of the novel visualization, in accordance with at least one embodiment of the invention.

In conjunction with the various statistical outputs of the invention described herein, there is also described herein a novel visualization technique to present the results in a succinct manner for quick clinical utilization. This visualization presents the results of patient-specific risk scores in a "bullseye" format with an overlaying "spider-web" that allows quick dissemination of the relative risk of a patient for each risk factor, an example of which is shown in FIG. 9. Additionally, this visualization is interactive, meaning a clinician can click on any risk factor within the visualization and information concerning which drugs in the patient's regimen contribute to the risk of that particular clinical factor is presented. Even further, the area of the "spider-web" of the chart is directly related to the overall risk of the patient's medication regime in a manner similar to the Personalized Medication Risk Score. The reason for this is based on the fact that varying various risk factors' risk scores will distort the "web" in degrees that could result in the clinician not being able to disseminate quickly which regimen change is better in terms of medication risk and patient health. However, by comparing the area of the visualizations' risk factor "spider-web" for each possible regimen change the clinician is considering, one can determine which recommendation would provide the best risk-lowering effect.

Application of the Algorithm and its Results

The ability to generate a total risk score for a patient is a highly valuable clinical tool for healthcare professionals. By providing a medication perspective that is deeper than what is traditionally evident within at a patient's chart, clinicians can better understand the overall healthcare of a patient. The accompanying visualization of the results allow a healthcare professional to quickly identify potential negative impacts of a patient's drug regimen and act quickly and efficiently to correct these negative impacts, as shown in FIG. 10.

However, this is only one aspect of the value of this presented medication risk stratification software. To elaborate, embodiments of this invention are able to generate total risk scores for as many patients as the medication data encompasses. For example, some embodiments currently have successfully analyzed the data of over 800,000 patients. By generating total risk scores as well as individual risk factor scores for all patients in a population, the embodiments are able to elucidate risk distributions within a population and thus elucidate the high risk patients within a large population size. The application of doing so allows healthcare and healthcare management professionals to quickly identify the patients within the population who need medical attention the most in terms of health risk and management. Once the members at high risk within a population are identified, the individual's scores can be scrutinized and medication risk mitigation can commence quickly and efficiently. Thus, at least some embodiments of the invention described herein allow a novel and accurate method of healthcare that incorporates big data analytics, clinically-driven scientific discovery and enhanced individual healthcare on a level that the industry has yet to perceive or implement.

Figure 11:
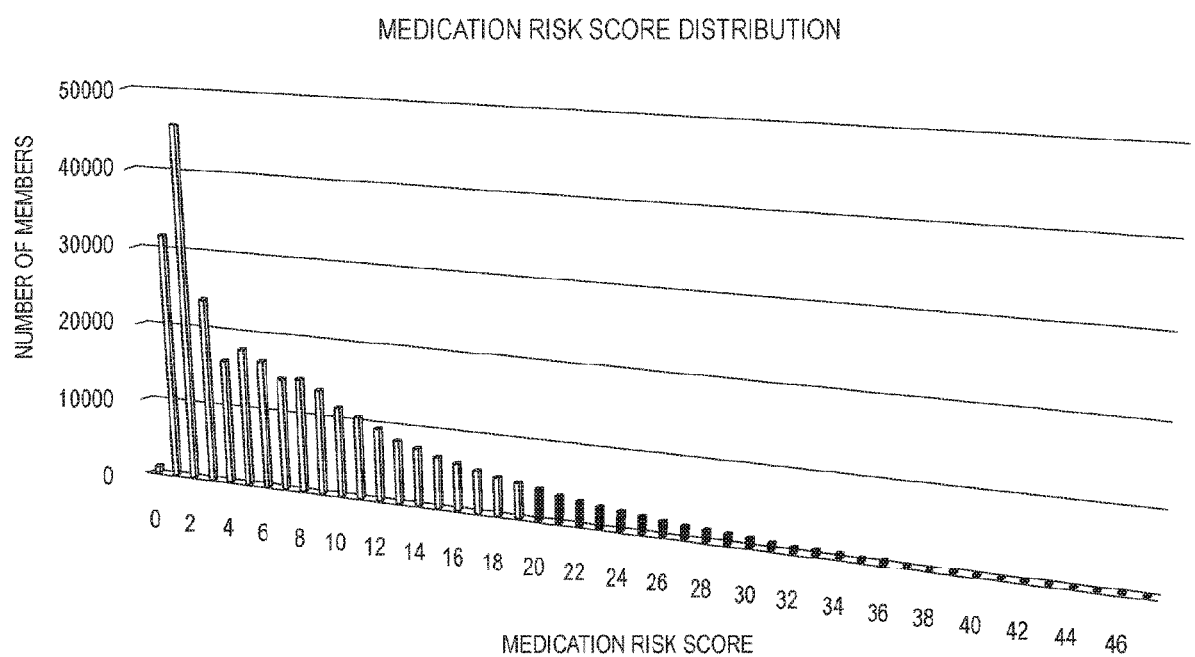
FIG. 11 is a graphic illustrating the Medication Risk Score distribution output graphic for 320,000 patients analyzed, in accordance with at least one embodiment of the invention.

FIG. 11 is a graphic illustrating the Medication Risk Score distribution output graphic for 320,000 patients analyzed. The y-axis describes the number of subject presenting with a particular risk score (x-axis). Note that the distribution is skewed to the left with less members presenting with high (>20) values.

Figure 12:
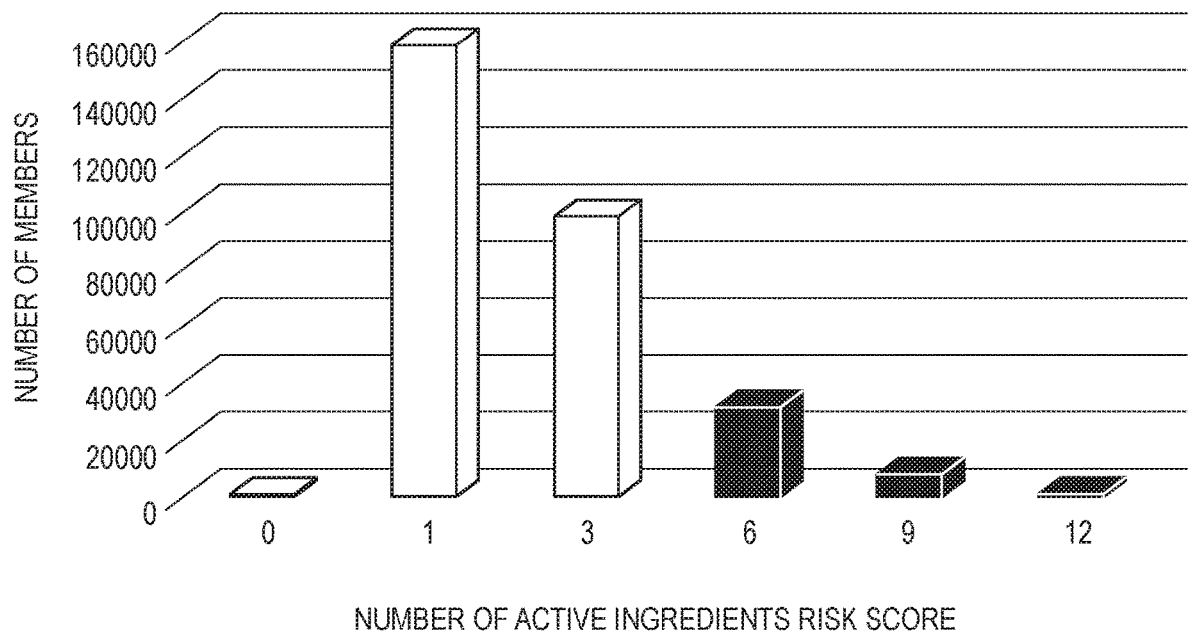
FIG. 12 is a graphic illustrating the Number of Active Ingredients (Factor 1) score distribution output graphic for 320,000 patient analysis.

FIG. 12 is a graphic illustrating the Number of Active Ingredients (Factor 1) score distribution output graphic for 320,000 patient analysis. Several patients were identified with a Number of Active Ingredients Risk score in the low risk range. At the same time, some patients were identified with a High Risk value (Number of Active Ingredients Risk Score greater than 6).

Figure 13:
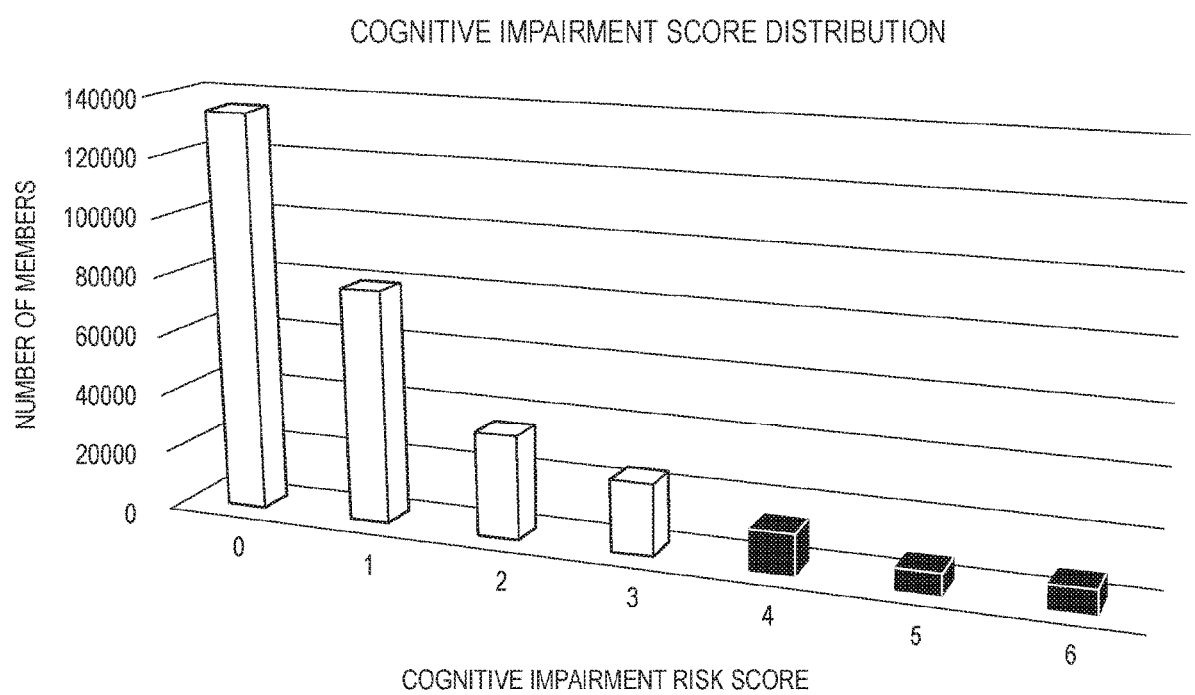
FIG. 13 is a graphic illustrating the Cognitive Impairment (Factor 2) score distribution output graphic for 320,000 patient analysis.

FIG. 13 is a graphic illustrating the Cognitive Impairment (Factor 2) score distribution output graphic for 320,000 patient analysis. Based on the developed algorithms and weighted risk evaluation in the invention described herein, patients with a Cognitive Impairment Risk Score greater than 4 were identified at high risk.

Figure 14:
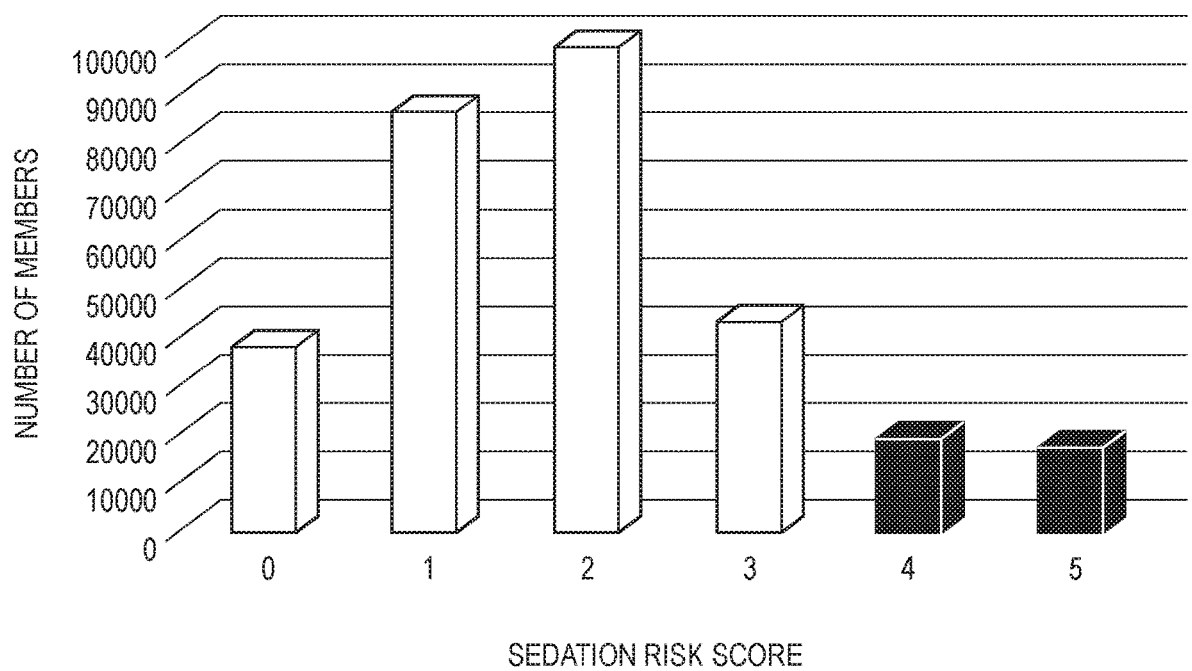
FIG. 14 is a graphic illustrating the Sedation impairment (Factor 3) score distribution output graphic for 320,000 patient analysis.

FIG. 14 is a graphic illustrating the Sedation Impairment (Factor 3) score distribution output graphic for 320,000 patient analysis. Based on the developed algorithms and weighted risk evaluation in the invention described herein, patients with a Sedation Impairment Risk Score greater than 4 were identified at high risk.

Figure 15:
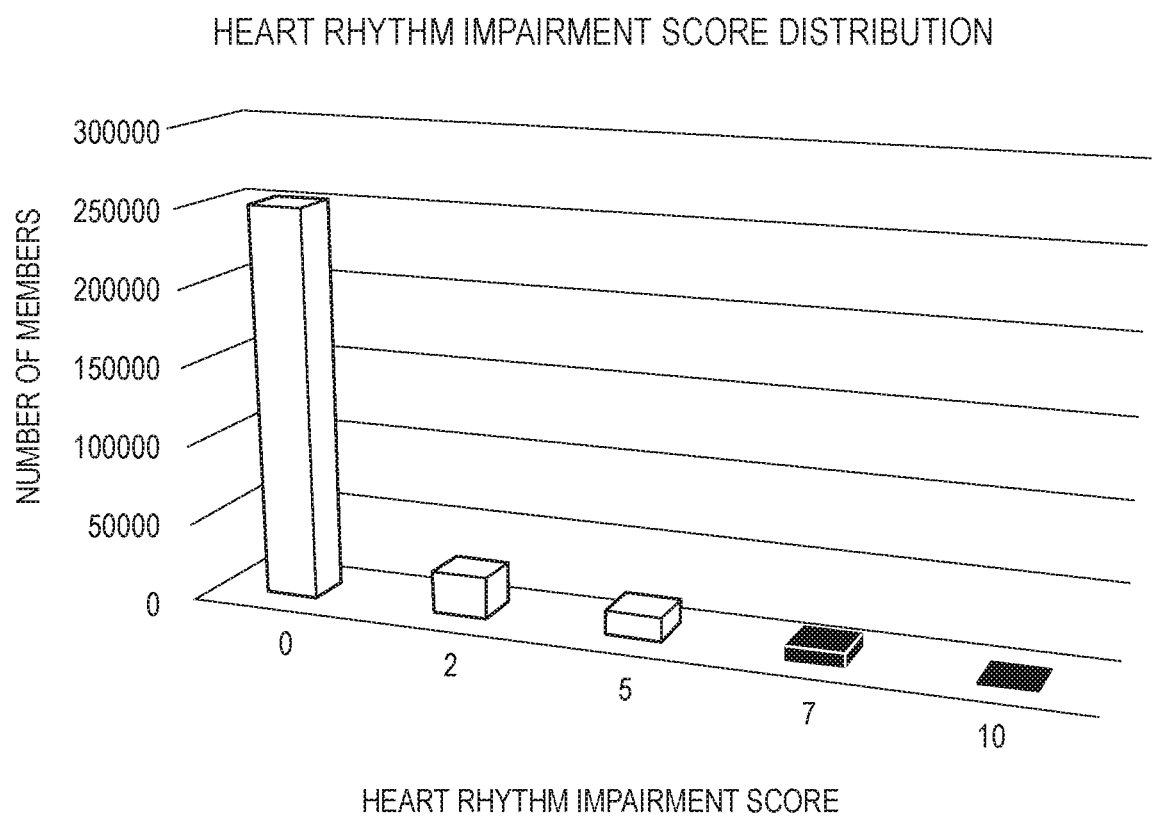
FIG. 15 is a graphic illustrating the Heart rhythm impairment (Factor 4) score distribution output graphic for 320,000 patient analysis.

FIG. 15 is a graphic illustrating the Heart Rhythm Impairment (Factor 4) score distribution output graphic for 320,000 patient analysis. Torsade de pointes is a major rhythm disorder observed in 0.16% of the population. The distribution of the Heart Rhythm Impairment Score illustrate this average distribution and allows to identify patients at high risk of this potentially lethal adverse drug event. A Score greater than 7, considering the Long QT-JT index and other risk factors (Long QT-JT score) allows to identify patients at the greatest risk.

Figure 16:
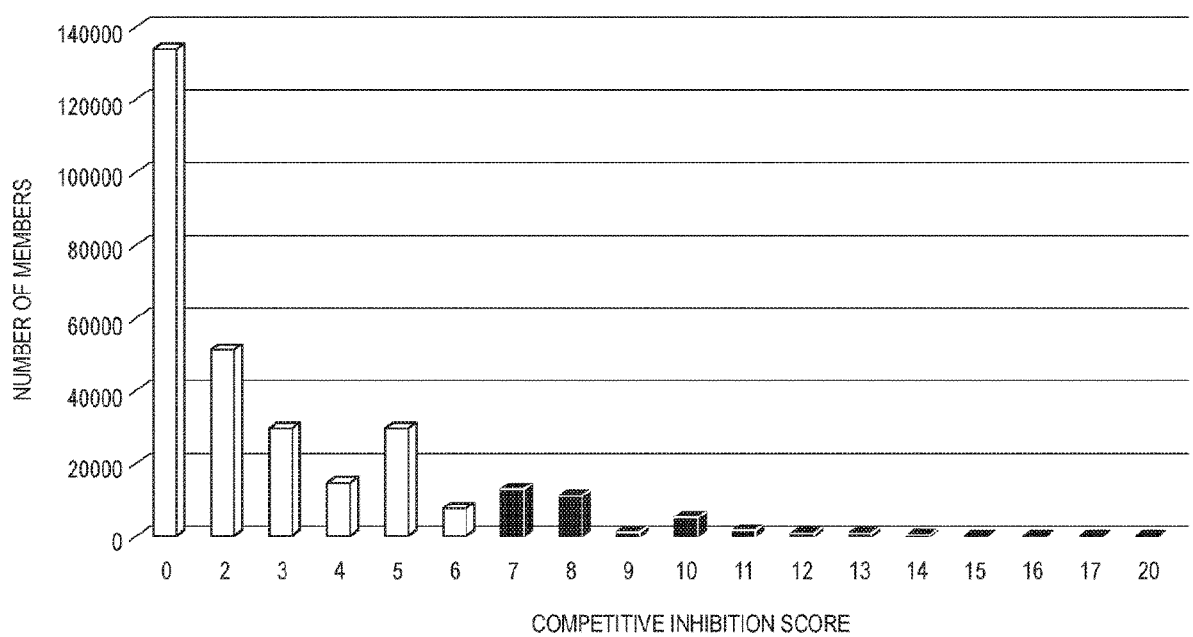
FIG. 16 is a graphic illustrating the Competitive inhibition (Factor 5) score distribution output graphic for 320,000 patient analysis.

FIG. 16 is a graphic illustrating the Competitive inhibition (Factor 5) score distribution output graphic for 320,000 patient analysis. Based on the appropriate computation and ranking of multi-drug interactions between inhibitors and substrates, inducers and substrates, and between substrates and substrates, a risk score is derived. Patients with a Competitive Inhibition risk score greater than 7 identifies patients at increased risk of multi-drug interactions.

Computer Implementation

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

Figure 17:
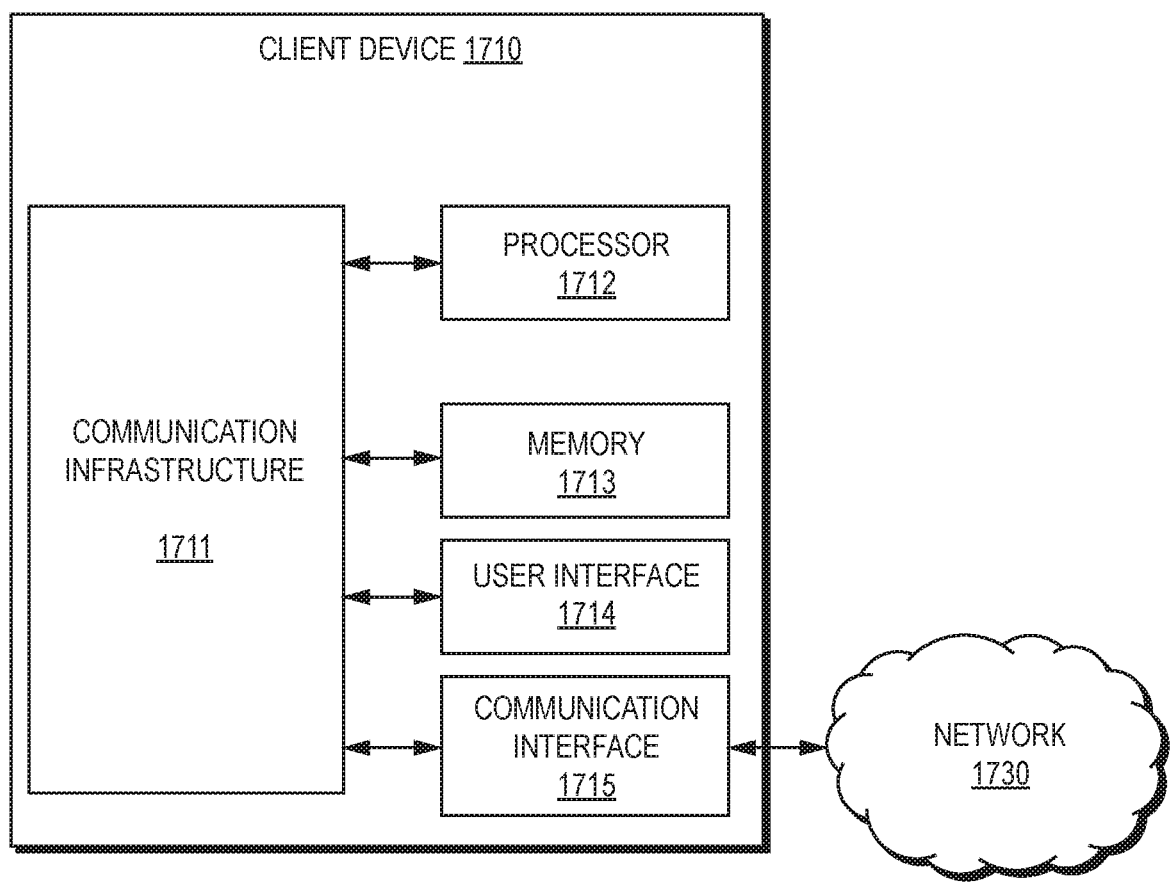
FIG. 17 shows a block diagram that illustrates a computer system 1700 for analyzing pharmacological characteristics of medication and patient's drug regimen data to generate new population based medication risk stratification and a personalized medication risk score, according to at least one embodiment of the invention.

FIG. 17 shows a block diagram that illustrates a system 1700 for analyzing pharmacological characteristics of medication and patient's drug regimen data to generate new population based medication risk stratification and a personalized medication risk score, according to at least one embodiment of the invention. In at least one embodiment, the system 1700 may include one or more computers or servers, non-transitory memory operable to store one or more computer programs and one or more processors to implement the one or more computer programs. For example, the system 1700, shown in FIG. 17, may include client device 1710 and network 130.

Client device 1710 may be a computing device for receiving inputs from a user, requesting data from a server device via network 1730 and/or displaying data at the request of a user. Examples of a client device 110 may include a smart phone, tablet or a personal computer, among others. In one embodiment, client device 1710 may represent multiple client devices, each of which is capable of performing the functions specified for client device 1710.

Client device 1710 may include communication infrastructure 1711, processor 1712, memory 1713, user interface 1714 and communication interface 1715.

Processor 1712 may be any type of processor, including but not limited to a special purpose or a general-purpose processor. Processor 112 may be connected to a communication infrastructure 1711 (for example, a bus or network) that also connects memory 1713, user interface 1714 and communications interface 1715. Various software implementations are described in terms of this exemplary computer system.

Memory 1713 may include at least one of: random access memory (RAM), a hard disk drive and a removable storage drive, such as a floppy disk drive, a magnetic tape drive, or an optical disk drive, etc. The removable storage drive reads from and/or writes to a removable storage unit. The removable storage unit can be a floppy disk, a magnetic tape, an optical disk, etc., which is read by and written to a removable storage drive. Memory 1713 may include a computer usable storage medium having stored therein computer software programs and/or data to perform any of the computing functions of client device 1710. Computer software programs (also called computer control logic), when executed, enable client device 1710 to implement embodiments of the invention as described herein. Accordingly, such computer software programs represent a controller of client device 1710.

User interface 1714 may be a program that controls a display (not shown) of client device 1710. User interface 1714 may include one or more peripheral user interface components, such as a keyboard or a mouse. The user may use the peripheral user interface components to interact with client device 1710. User interface 1714 may receive user inputs, such as mouse inputs or keyboard inputs from the mouse or keyboard user interface components.

Communication interface 1715 allows data to be transferred between client device 1710 and external devices. Examples of communication interface 115 may include a modem, a network interface (such as an Ethernet card), a communication port, a Personal Computer Memory Card International Association (PCMCIA) slot and card, etc. Data transferred via communication interface 1715 are in the form of signals, which may be electronic, electromagnetic, optical, or other signals capable of being transmitted or received by communication interface. These signals are provided to or received from communication interface 1715 via network 1730.

Network 1730 connects client device 1710 to external devices by carrying signals. Network 1730 may be implemented using wire or cable, fiber optics, a phone line, a wireless link, a cellular phone link, a radio frequency link, or any other suitable communication channel. For instance, network 1730 may be implemented using a combination of channels. Network 1730 may be implemented as an intranet and/or an internet.

Methods of Treating a Patient Identified as High-Risk as Described Herein

In an embodiment, the invention includes a method of treating patients who are identified as being at high risk for an adverse drug event.

In some embodiments, the method may include the step of determining whether the patient is at high risk of the adverse drug event according to the methods disclosed herein, wherein the patient has been prescribed a drug regimen that includes at least a first drug and a second drug. In some embodiments, the patient's drug regimen includes at least 3 drugs, 4 drugs, 5, drugs, 6 drugs, 7 drugs, 8 drugs, 9 drugs, 10 drugs, 11 drugs, 12 drugs, 13 drugs, 14 drugs, or 15 drugs; or includes less than 3 drugs, 4 drugs, 5, drugs, 6 drugs, 7 drugs, 8 drugs, 9 drugs, 10 drugs, 11 drugs, 12 drugs, 13 drugs, 14 drugs, or 15 drugs; or about 3 drugs, 4 drugs, 5, drugs, 6 drugs, 7 drugs, 8 drugs, 9 drugs, 10 drugs, 11 drugs, 12 drugs, 13 drugs, 14 drugs, or 15 drugs.

In some embodiments, the method may include one or more of the steps of:
  (a) removing the first drug and/or the second drug from the patient's drug regimen;
  (b) reordering which of the first drug and the second drug is taken first by the patient;
  (c) changing the timing of when the first drug and/or the second drug are taken by the patient;
  (d) changing the time of day when the first drug and/or the second drug are taken by the patient;
  (e) replacing the first drug and/or the second drug of the patient's drug regimen with one or more alternate drugs of the same class and/or category as the first drug and/or the second drug;
  (f) reducing the dosage of the first drug and/or the second drug from an initial dosage to a reduced dosage;
  (g) increasing the dosage of the first drug and/or the second drug from an initial dosage to an increased dosage;

(h) performing a surgical procedure; and
(i) adding at least a third drug to the patient's drug regimen;
wherein the one or more foregoing steps are provided to reduce the patient's risk of the adverse drug event.

In some embodiments, the step of removing the first drug and/or the second drug from the patient's drug regimen may include removing a plurality of drugs from the patient's drug regimen. In some embodiments, the method may further include the step of recalculating whether the patient is at high risk for developing an adverse drug event after the first drug and/or the second drug are removed from the patient's drug regimen.

In some embodiments, the step of reordering which of the first drug and the second drug is taken first by the patient may include instructing the patient to take the first drug before the second drug. In some embodiments, the step of reordering which of the first drug and the second drug is taken first by the patient may include instructing the patient to take, or administering, the second drug before the first drug. In some embodiments, the method may further include the step of recalculating whether the patient is at high risk for developing an adverse drug event after the reordering of the first drug and/or the second drug.

In some embodiments, the step of changing the timing of when the first drug and/or the second drug are taken by the patient may include increasing the period between drug doses by at least at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, or 7 days; increasing the period between drug doses by less than 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, or 7 days; increasing the period between drug doses by about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, or 7 day. In some embodiments, the step of changing the timing of when the first drug and/or the second drug are taken by the patient may include decreasing the period between drug doses by at least at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, or 7 days; decreasing the period between drug doses by less than 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, or 7 day. In some embodiments, the method may further include the step of recalculating whether the patient is at high risk for developing an adverse drug event after the timing of the first drug and/or the second drug is changed.

In some embodiments, the step of changing the time of day when the first drug and/or the second drug are taken by the patient may include switching an AM or morning administration to a PM or evening administration; or by switching a PM or evening administration to an AM or morning administration; or by switching a morning administration to an afternoon administration; or by switching an evening administration to an afternoon administration; or by switching an afternoon administration to a morning administration; or by switching an afternoon administration to an evening administration of the first and/or the second drug. In some embodiments, the method may further include the step of recalculating whether the patient is at high risk for developing an adverse drug event after the time of day when the first drug and/or the second drug are taken is changed.

In some embodiments, replacing the first drug and/or the second drug of the patient's drug regimen with one or more alternate drugs of the same class and/or category includes replacing the first drug with one or more alternate drugs of the same class and/or category. In some embodiments, replacing the first drug and/or the second drug of the patient's drug regimen with one or more alternate drugs of the same class and/or category includes replacing the second drug with one or more alternate drugs of the same class and/or category. In some embodiments, replacing the first drug and/or the second drug of the patient's drug regimen with one or more alternate drugs of the same class and/or category includes replacing the first drug and the second drug with one or more alternate drugs of the same class and/or category In some embodiments, the method may further include the step of recalculating whether the patient is at high risk for developing an adverse drug event after the first drug and/or the second drug are replaced with one or more alternate drugs of the same class and/or category.

In some embodiments, where the method includes the step of reducing the dosage of the first drug and/or the second drug from an initial dosage to a reduced dosage, the reduced dosage may be greater than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of the initial dosage. In some embodiments, the reduced dosage may be less than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of the initial dosage. In some embodiments, the reduced dosage may be about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of the initial dosage. In some embodiments, the method may further include the step of recalculating whether the patient is at high risk for developing an adverse drug event after the dosage of the first drug and/or the second drug have been reduced from the initial dosage to the reduced dosage.

In some embodiment, the where the method includes the step of increasing the dosage of the first drug and/or the second drug from an initial dosage to an increased dosage, the initial dosage may be greater than 500%, 400%, 300%, 200%, 175%, 150%, 125%, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of the increased dosage. In some embodiments, the initial dosage may be less than 500%, 400%, 300%, 200%, 175%, 150%, 125%, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of the increased dosage. In some embodiments, the initial dosage may be about 500%, 400%, 300%, 200%, 175%, 150%, 125%, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of the increased dosage. In some embodiments, the method may further include the step of recalculating whether the patient is at high risk for developing an adverse drug event after the dosage of the first drug and/or the second drug have been increased from the initial dosage to the increased dosage.

In some embodiments, the step of adding at least a third drug to the patient's drug regimen includes adding at least 3 drugs, 4 drugs, 5, drugs, 6 drugs 7 drugs, 8 drugs, 9 drugs, 10 drugs, 11 drugs, 12 drugs, 13 drugs, 14 drugs, or 15 drugs; or includes less than 3 drugs, 4 drugs, 5, drugs, 6 drugs, 7 drugs, 8 drugs, 9 drugs, 10 drugs, 11 drugs, 12 drugs, 13 drugs, 14 drugs, or 15 drugs; or about 3 drugs, 4 drugs, 5, drugs, 6 drugs 7 drugs, 8 drugs, 9 drugs, 10 drugs, 11 drugs, 12 drugs, 13 drugs, 14 drugs, or 15 drugs to the patient's drug regiment wherein such drug(s) are added to alleviate the patient's high risk for developing an adverse drug event. In some embodiments, the method may further include the step of recalculating whether the patient is at high risk for developing an adverse drug event after at least the third drug is added to the patient's drug regimen. In some embodiments, the third drug is in the same class and/or category as the first drug and/or the second drug. In some embodiments, the third drug is in a different class and/or category as the first drug and/or the second drug.

In some embodiments of the methods described herein, a patient is determined to be at high risk due to a risk score associated with one or more of
  (1) the number of medications (drugs) in the patient's drug regimen (i.e., Factor 1);
  (2) the patient's cognitive impairment (i.e., Factor 2);
  (3) the patient's sedative impairment (i.e., Factor 3);
  (4) the patient's heart rhythm impairment (i.e., Factor 4); and
  (5) the patient's competitive inhibition (i.e., Factor 5).

In some embodiments of the methods described herein, a patient is determined to be high risk due to an aggregate risk score determined by analyzing:
  (1) the number of medications (drugs) in the patient's drug regimen (i.e., Factor 1);
  (2) the patient's cognitive impairment (i.e., Factor 2);
  (3) the patient's sedative impairment (i.e., Factor 3);
  (4) the patient's heart rhythm impairment (i.e., Factor 4); and
  (5) the patient's competitive inhibition (i.e., Factor 5).

In an embodiment, the invention may include a method of altering the ordering and/or timing of drug delivery and dosing thereof to patients with a drug regimen in order to manage, control, and predict harmful drug interactions and interactions between such drugs and the patient's body (e.g., effect of drug, drugs, or drug combinations, on the CYP450 superfamily).

In an embodiment, the invention may include a method provided to avoid having two drugs, which are substrates of the same isoenzyme, being present or delivered at high concentrations in the liver and/or the intestine at the same time or within the same time interval. In some embodiments, the methods described herein include step of delivering first the drug (of the two or more substrates) with the lowest affinity for the isoenzyme before delivering those other drugs having a higher affinity for the isoenzyme.

In some embodiments, the methods may include the step of determining the Tmax of the drug with the lowest affinity for the isoenzyme.

In some embodiments, the methods may include the step of delivering the drug with the highest affinity for the isoenzyme with a delay equal to or greater than the Tmax of the low affinity drug described hereinabove.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one". As used herein, the term "about" may refer to +or −10% of the value referenced. For example, "about 9" is understood to encompass 8.2 and 9.9.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the invention described herein should not be limited to the performance of their steps in the order written, and one skilled in the art can readily appreciate that the steps may be varied and still remain within the spirit and scope of the invention described herein.

What is claimed is:

1. A computer-implemented method for determining and reducing a patient's risk of an adverse drug event in a patient diagnosed with pain, wherein the patient has been prescribed a drug regimen that includes at least an opioid for treating pain and a second drug, the method comprising:

calculating, with a calculating module, a quantitative personalized medication total risk score for multi-drug interaction for the patient that is representative of the patient's risk for an adverse drug event by:

(a) aggregating and weighting risk factor scores for risk factors associated with the patient's drug regimen including at least the opioid for treating pain and the second drug onto a common scale to produce aggregated risk factor scores, wherein the risk factors comprise:

(1) Factor 1: number of active ingredients in the patient's drug regimen including at least the opioid for treating pain and the second drug, wherein calculating the aggregated risk factor score representative of the number of active ingredients in the drug regimen comprises importing a data set comprising patient-specific drug regimens, converting said data set into respective active ingredients, quantifying the number of active ingredients each patient-specific regimen contains, and assigning the risk factor score representative of the number of active ingredients in the drug regimen, wherein the aggregated risk factor score representative of the number of active ingredients in the drug regimen is less than or equal to 12, (2) Factor 2: anticholinergic burden of the patient's drug regimen including at least the opioid for treating pain and the second drug, wherein calculating the aggregated risk factor score representative of the anticholinergic burden of the drug regimen comprises importing a data set comprising indices of anticholinergic burden, associating the respective active ingredients with their clinically determined anticholinergic value, quantifying the value for the entire respective regimen, and assigning the aggregated risk factor score representative of the anticholinergic burden of the drug regimen, wherein the aggregated risk factor score representative of the anticholinergic burden of the drug regimen is less than or equal to 6, (3) Factor 3: sedative burden of the patient's drug regimen including at least the opioid for treating pain and the second drug, wherein calculating the aggregated risk factor score representative of the sedative burden of the drug regimen comprises importing a data set comprising indices of sedation effects, associating the respective active ingredients with their clinically determined sedation value, quantifying the value for the entire respective regimen, and assigning the aggregated risk factor score representative of the sedative burden of the drug regimen, wherein the aggregated risk factor score representative of the sedative burden of the drug regimen is less than or equal to 5, (4) QT-interval prolongation risk of the patient's drug regimen including at least the opioid for treating pain and the second drug, wherein calculating the aggregated risk factor score representative of the QT-interval prolongation risk of the drug regimen comprises importing a data set comprising indices of QT-prolongation risk, associating the respective active ingredients with their clinically determined QT-risk value, quantifying the value for the entire respective regimen, and assigning the aggregated risk factor score representative of the QT-interval prolongation risk of the drug regimen, wherein the aggregated risk factor score representative of the QT-interval prolongation risk of the drug regimen is less than or equal to 10, and (5) competitive inhibition of the patient's drug regimen including at least the opioid for treating pain and the second drug, wherein calculating the aggregated risk factor score representative of the competitive inhibition of the drug regimen comprises importing a data set comprising metabolic pathways and extent of metabolism for each active ingredient, associating the respective ingredients with competitive inhibition values based on shared pathways, quantifying the competitive inhibition value for the entire respective regimen, and assigning the aggregated risk factor score representative of the competitive inhibition of the drug regimen; and (b) calculating, with the calculating module, the patient's quantitative personalized medication risk score by combining the aggregated and weighted risk factor scores representative of each of the risk factors associated with the patient's drug regimen including at least the opioid for treating pain and the second drug;

(c) identifying the calculated quantitative personalized medication total risk score as falling below a threshold value and thereby falling within a low-risk group or as falling above the threshold value and thereby falling within a high-risk group;

generating a prognosis for the patient having pain as being within the high-risk group as being a high-risk patient for an adverse drug event if the patient's calculated quantitative personalized medication total risk score is identified as falling within the high-risk group; and adjusting the high-risk patient's drug regimen including at least the opioid for treating pain and the second drug to decrease the patient's calculated quantitative personalized medication total risk score such that the high-risk patient's risk of an adverse drug event is reduced; and such that treatment of the patient's pain is improved by performing one or more steps of:

(a) reordering which of the opioid for treating pain and the second drug is taken first by the patient;

(b) changing timing of when the opioid for treating pain and/or the second drug are taken by the patient;

(c) changing time of day when the opioid for treating pain and/or the second drug are taken by the patient;

(d) replacing the opioid for treating pain and/or the second drug of the patient's drug regimen with one or more alternate drugs of the same class and/or category as the opioid for treating pain and/or the second drug;

(e) reducing a dosage of the opioid for treating pain and/or the second drug from an initial dosage to a reduced dosage;

(f) increasing a dosage of the opioid for treating pain and/or the second drug from an initial dosage to an increased dosage;

(g) adding at least a third drug to the patient's drug regimen including at least the opioid for treating pain and the second drug; and (h) replacing the opioid for treating pain and/or the second drug of the patient's drug regimen including at least the opioid for treating pain and the second drug with one or more alternate drugs of a different class and/or category as the opioid for treating pain and/or the second drug; and administering to the high-risk patient the adjusted drug regimen to decrease the patient's calculated quantitative personalized medication total risk score such that the high-risk patient's risk of an adverse drug event is reduced; and such that treatment of the patient's pain is improved.

2. The computer-implemented method according to claim 1, wherein the calculating module further generates a stratified data set representative of a patient population's risk of adverse drug events, the method comprising:

generating a second risk score based on one or both of (i) the number of the active ingredients, and (ii) side effects associated with the active ingredients; and generating a stratified data set representative of a patient population's risk of adverse drug events, the method comprising combining the patient's calculated quantitative personalized medication total risk score and the at least second risk scores for a plurality of patients within the patient population.

3. The computer-implemented system according to claim 2, wherein the calculating module assigns each of the plurality of patients within the stratified data set according to the patient's personalized medication risk score that is representative of the patient's risk for an adverse drug event from the patient's drug regimen.

4. The computer-implemented system according to claim 3, wherein the calculating module further identifies patients within the stratified data set as being at high risk for multi-drug interactions within the patient population.

5. The computer-implemented system according to claim 3, wherein the calculating module further calculates risk for each drug regimen of each patient within the patient population and generates a stratified data set representative of the risks of occurrence of adverse drug events due to particular drug regimens.

6. A method of reducing a risk of an adverse drug event in a patient having hypertension, wherein the patient has been prescribed a drug regimen that includes at least an antihypertensive and a second drug, the method comprising:

calculating a quantitative personalized medication risk score that is representative of the patient's risk for an adverse drug event by:

aggregating and weighting risk factor scores for risk factors associated with the patient's drug regimen including at least the antihypertensive for treating hypertension and the second drug onto a common scale to produce aggregated risk factor scores, wherein the risk factors comprise:

1) number of active ingredients in the drug regimen, wherein calculating the aggregated risk factor score representative of the number of active ingredients in the drug regimen comprises importing a data set comprising patient-specific drug regimens, converting said data set into respective active ingredients, quantifying the number of active ingredients each patient-specific regimen contains, and assigning the risk factor score representative of the number of active ingredients in the drug regimen, wherein the aggregated risk factor score representative of the number of active ingredients in the drug regimen is less than or equal to 12;

2) anticholinergic burden of the drug regimen, wherein calculating the aggregated risk factor score representative of the anticholinergic burden of the patient's drug regimen comprises importing a data set comprising indices of anticholinergic burden, associating the respective active ingredients with their clinically determined anticholinergic value, quantifying the value for the entire respective regimen, and assigning the aggregated risk factor score representative of the anticholinergic burden of the drug regimen, wherein the aggregated risk factor score representative of the anticholinergic burden of the drug regimen is less than or equal to 6;

3) sedative burden of the drug regimen, wherein calculating the aggregated risk factor score representative of the sedative burden of the drug regimen comprises importing a data set comprising indices of sedation effects, associating the respective active ingredients with their clinically determined sedation value, quantifying the value for the entire respective regimen, and assigning the aggregated risk factor score representative of the sedative burden of the drug regimen, wherein the aggregated risk factor score representative of the sedative burden of the drug regimen is less than or equal to 5;

4) QT-interval prolongation risk of the drug regimen, wherein calculating the aggregated risk factor score representative of the QT-interval prolongation risk of the drug regimen comprises importing a data set comprising indices of QT-prolongation risk, associating the respective active ingredients with their clinically determined QT-risk value, quantifying the value for the entire respective regimen, and assigning the aggregated risk factor score representative of the QT-interval prolongation risk of the drug regimen, wherein the aggregated risk factor score representative of the QT-interval prolongation risk of the drug regimen is less than or equal to 10; and 5) competitive inhibition of the drug regimen, wherein calculating the aggregated risk factor score representative of the competitive inhibition of the drug regimen comprises importing a data set comprising metabolic pathways and extent of metabolism for each active ingredient, associating the respective ingredients with competitive inhibition values based on shared pathways, quantifying the competitive inhibition value for the entire respective regimen, and assigning the aggregated risk factor score representative of the competitive inhibition of the drug regimen, wherein the aggregated risk factor score representative of the competitive inhibition of the drug regimen in the drug regimen is less than or equal to 20; and calculating, with the calculating module, the patient's quantitative personalized medication risk score by combining the aggregated and weighted risk factor scores representative of each of the risk factors associated with the patient's drug regimen including at least the antihypertensive and the second drug;

identifying the calculated quantitative personalized medication total risk score as falling below a threshold value and thereby falling within a low-risk group or as falling above the threshold value and thereby falling within a high-risk group;

generating a prognosis for the patient having pain as being within the high-risk group as being a high-risk patient for an adverse drug event if the patient's calculated quantitative personalized medication total risk score is identified as falling within the high-risk group; and adjusting the high-risk patient's drug regimen including at least the antihypertensive for treating hypertension and the second drug to decrease the patient's calculated quantitative personalized medication total risk score such that the high-risk patient's risk of an adverse drug event is reduced; and such that treatment of the patient's hypertension is improved by performing one or more steps of:

(a) reordering which of the antihypertensive for treating hypertension and the second drug is taken first by the patient;

(b) changing timing of when the antihypertensive for treating hypertension and/or the second drug are taken by the patient;

(c) changing time of day when the antihypertensive for treating hypertension first drug and/or the second drug are taken by the patient;

(d) replacing the antihypertensive for treating hypertension and/or the second drug of the patient's drug regimen with one or more alternate drugs of the same class and/or category as the antihypertensive for treating hypertension and/or the second drug;

(e) reducing the dosage of the antihypertensive for treating hypertension and/or the second drug from an initial dosage to a reduced dosage;

(f) increasing the dosage of the antihypertensive for treating hypertension and/or the second drug from an initial dosage to an increased dosage;

(g) replacing the antihypertensive for treating hypertension and/or the second drug of the patient's drug regimen including at least the antihypertensive for treating hypertension and the second drug with one or more alternate drugs of a different class and/or category as the antihypertensive for treating hypertension and/or the second drug; and (h) adding at least a third drug to the patient's drug regimen including at least the antihypertensive for treating hypertension and the second drug; and administering to the high-risk patient the adjusted drug regimen to decrease the patient's calculated quantitative personalized medication total risk score such that the high-risk patient's risk of an adverse drug event is reduced; and such that treatment of the patient's hypertension is improved.

7. The method according to claim 6, wherein calculating the quantitative personalized medication risk score comprises executing instructions stored on a non-transitory computer-readable medium.

8. The method according to claim 7 comprising using a computing device to execute the instructions stored on the non-transitory computer-readable medium.

9. The method according to claim 6 further comprising comparing the patient's quantitative personalized medication risk score for the drug regimen to quantitative personalized medication risk scores of a patient population for said drug regimen.

10. The method according to claim 6, wherein adjusting the patient's drug regimen causes the quantitative personalized medication risk score to decrease.

11. The method according to claim 6, wherein the calculating module further generates a stratified data set representative of a patient population's risk of adverse drug events, the method comprising:

generating a second risk score based on one or both of (i) the number of the active ingredients, and (ii) side effects associated with the active ingredients; and generating a stratified data set representative of a patient population's risk of adverse drug events, the method comprising combining the patient's calculated quantitative personalized medication total risk score and the at least second risk scores for a plurality of patients within the patient population.

12. A method for determining and reducing a patient's risk of an adverse drug event in a patient diagnosed with depression, wherein the patient diagnosed with depression has been prescribed a drug regimen that includes at least an antipsychotic and a second drug, the method comprising:

(a) collecting a first data set comprising the drug regimen for the patient diagnosed with depression via a user interface;

(b) determining active ingredients in the patient-specific drug regimen by comparing the first data set with a second data set stored in a connected, non-transitory computer-readable storage medium, the second data set correlating drug names with active ingredients;

(c) calculating a quantitative personalized medication total risk score for multi-drug interaction for the patient that is representative of the patient's risk for an adverse drug event by: aggregating and weighting risk factor scores for risk factors associated with the patient's drug regimen including at least the antipsychotic and the second drug onto a common scale to produce aggregated risk factor scores, wherein the risk factors comprise:

1) number of active ingredients in the drug regimen, wherein calculating the aggregated risk factor score representative of the number of active ingredients in the drug regimen comprises importing a data set comprising patient-specific drug regimens, converting said data set into respective active ingredients, quantifying the number of active ingredients each patient-specific regimen contains, and assigning the risk factor score representative of the number of active ingredients in the drug regimen, wherein the aggregated risk factor score representative of the number of active ingredients in the drug regimen is less than or equal to 12;

2) anticholinergic burden of the drug regimen, wherein calculating the aggregated risk factor score representative of the anticholinergic burden of the drug regimen comprises importing a data set comprising indices of anticholinergic burden, associating the respective active ingredients with their clinically determined anticholinergic value, quantifying the value for the entire respective regimen, and assigning the aggregated risk factor score representative of the anticholinergic burden of the drug regimen, wherein the aggregated risk factor score representative of the number of active ingredients in the drug regimen is less than or equal to 6;

3) sedative burden of the drug regimen, wherein calculating the aggregated risk factor score representative of the sedative burden of the active ingredients in the drug regimen comprises importing a data set comprising indices of sedation effects, associating the respective active ingredients with their clinically determined sedation value, quantifying the value for the entire respective regimen, and assigning the aggregated risk factor score representative of the sedative burden of the drug regimen, wherein the aggregated risk factor score representative of the number of active ingredients in the drug regimen is less than or equal to 5;

4) QT-interval prolongation risk of the drug regimen, wherein calculating the aggregated risk factor score representative of the QT-interval prolongation risk of the active ingredients in the drug regimen comprises importing a data set comprising indices of QT-prolongation risk, associating the respective active ingredients with their clinically determined QT-risk value, quantifying the value for the entire respective regimen, and assigning the aggregated risk factor score representative of the QT-interval prolongation risk of the drug regimen, wherein the aggregated risk factor score representative of the number of active ingredients in the drug regimen is less than or equal to 10; and 5) competitive inhibition of the drug regimen, wherein calculating the aggregated risk factor score representative of the competitive inhibition of the drug regimen comprises importing a data set comprising metabolic pathways and extent of metabolism for each active ingredient, associating the respective ingredients with competitive inhibition values based on shared pathways, quantifying the competitive inhibition value for the entire respective regimen, and assigning the aggregated risk factor score representative of the competitive inhibition of the drug regimen, wherein the aggregated risk factor score representative of the number of active ingredients in the drug regimen is less than or equal to 20; and calculating, with the calculating module, the patient's quantitative personalized medication risk score by combining the aggregated and weighted risk factor scores representative of each of the risk factors associated with the patient's drug regimen including at least the antipsychotic and the second drug;

identifying the calculated quantitative personalized medication total risk score as falling below a threshold value and thereby falling within a low-risk group or as falling above the threshold value and thereby falling within a high-risk group;

generating a prognosis for the patient having pain as being within the high-risk group as being a high-risk patient for an adverse drug event if the patient's calculated quantitative personalized medication total risk score is identified as falling within the high-risk group; and adjusting the high-risk patient's drug regimen including at least the antipsychotic for treating depression and the second drug to decrease the patient's calculated quantitative personalized medication total risk score such that the high-risk patient's risk of an adverse drug event is reduced; and such that treatment of the patient's depression is improved by performing one or more steps of:

(a) reordering which of the antipsychotic for treating depression and the second drug is taken first by the patient;

(b) changing timing of when the antipsychotic for treating depression and/or the second drug are taken by the patient;

(c) changing time of day when the antipsychotic for treating depression and/or the second drug are taken by the patient;

(d) replacing the antipsychotic for treating depression and/or the second drug of the patient's drug regimen with one or more alternate drugs of the same class and/or category as the antipsychotic for treating depression and/or the second drug;

(e) reducing a dosage of the antipsychotic for treating depression and/or the second drug from an initial dosage to a reduced dosage;

(f) increasing a dosage of the antipsychotic for treating depression and/or the second drug from an initial dosage to an increased dosage;

(g) adding at least a third drug to the patient's drug regimen including at least the antipsychotic for treating depression and the second drug; and (h) replacing the antipsychotic for treating depression and/or the second drug of the patient's drug regimen including at least the antipsychotic for treating depression and the second drug with one or more alternate drugs of a different class and/or category as the antipsychotic for treating depression and/or the second drug; and administering to the high-risk patient the adjusted drug regimen to decrease the patient's calculated quantitative personalized medication total risk score such that the high-risk patient's risk of an adverse drug event is reduced; and such that treatment of the patient's depression is improved.

13. The method according to claim 12, further comprising:

generating a second risk score based on one or both of (i) the number of the active ingredients, and (ii) side effects associated with the active ingredients; and generating a stratified data set representative of a patient population's risk of adverse drug events, the method comprising combining the patient's calculated quantitative personalized medication total risk score and the at least second risk scores for a plurality of patients within the patient population.

14. The method according to claim 12, the method further comprising providing the personalized medication risk score as a visual representation of a relative risk of each of said risk factors with respect to each other.

15. A processor configured to implement the method according to claim 12, wherein the processor is connected to the non-transitory computer-readable medium.

16. A client device comprising:
a processor configured to implement the method according to claim 12, wherein the processor is connected to the non-transitory computer-readable medium,
a communication infrastructure,
a memory, a user interface, and a communication interface.

17. A system comprising one or more computing devices, the one or more computing devices comprising one or more processors configured to implement the method according to claim 12, wherein the one or more processors are connected to the non-transitory computer-readable medium.

\* \* \* \* \*